US009079884B2

(12) United States Patent
Cesco-Cancian et al.

(10) Patent No.: US 9,079,884 B2
(45) Date of Patent: Jul. 14, 2015

(54) PROCESS FOR THE PREPARATION OF SUBSTITUTED PYRIMIDINE DERIVATIVES

(71) Applicant: Janssen Pharmaceutica NV, New Brunswick, NJ (US)

(72) Inventors: Sergio Cesco-Cancian, Bethlehem, PA (US); Hongfeng Chen, Somerville, NJ (US); Jeffrey S. Grimm, Somerville, NJ (US); Neelakandha S. Mani, San Diego, CA (US); Christopher M. Mapes, La Jolla, CA (US); David C. Palmer, Doylestown, PA (US); Daniel J. Pippel, Del Mar, CA (US); Kirk L. Sorgi, Doylestown, PA (US); Tong Xiao, Edison, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/076,955

(22) Filed: Nov. 11, 2013

(65) Prior Publication Data
US 2014/0066624 A1     Mar. 6, 2014

Related U.S. Application Data

(62) Division of application No. 13/844,227, filed on Mar. 15, 2013, which is a division of application No. 13/663,233, filed on Oct. 29, 2012, which is a division of application No. 12/459,229, filed on Jun. 29, 2009, now Pat. No. 8,309,720.

(60) Provisional application No. 61/076,752, filed on Jun. 30, 2008.

(51) Int. Cl.
C07D 401/12     (2006.01)
C07D 211/22     (2006.01)
C07D 211/26     (2006.01)

(52) U.S. Cl.
CPC ............ *C07D 401/12* (2013.01); *C07D 211/22* (2013.01); *C07D 211/26* (2013.01)

(58) Field of Classification Search
CPC .................................................... C07D 401/12
USPC ........................................................ 544/330
See application file for complete search history.

(56) References Cited

U.S. PATENT DOCUMENTS

| | | | |
|---|---|---|---|
| 3,005,852 A | 10/1961 | Freyermuth | |
| 3,931,195 A | 1/1976 | Dykstra et al. | |
| 4,190,601 A | 2/1980 | Decker et al. | |
| 4,191,828 A | 3/1980 | Horgan et al. | |
| 5,621,097 A | 4/1997 | Brown | |
| 6,372,743 B1 | 4/2002 | Darrow et al. | |
| 6,693,194 B2 | 2/2004 | Jau | |
| 6,835,726 B2 | 12/2004 | Cushing et al. | |
| 6,916,938 B2 | 7/2005 | Oguma | |
| 7,507,737 B2 | 3/2009 | Edwards et al. | |
| 8,309,709 B2 * | 11/2012 | Berg et al. ...................... 536/124 |
| 8,309,720 B2 * | 11/2012 | Cesco-Cancian et al. ..... 544/330 |
| 2004/0224964 A1 | 11/2004 | O'Yang et al. | |
| 2013/0053561 A1 | 2/2013 | Cesco-Cancian | |
| 2013/0225816 A1 | 8/2013 | Cesco-Cancian | |

FOREIGN PATENT DOCUMENTS

| | | |
|---|---|---|
| JP | 61030576 A | 2/1986 |
| JP | 1996-502486 | 4/1994 |
| JP | 2003-502406 | 12/2000 |
| WO | WO99/41253 | 8/1999 |
| WO | WO02/064096 | 8/2002 |
| WO | WO 02/078701 A1 | 10/2002 |
| WO | WO2006/138304 | 12/2006 |
| WO | WO 2007/092095 A | 8/2007 |
| WO | WO2007/117400 | 10/2007 |
| WO | WO2010/002774 | 1/2010 |

OTHER PUBLICATIONS

U.S. Appl. No. 14/078,153, filed Nov. 12, 2013, Cesco-Cancian.
U.S. Appl. No. 14/079,358, filed Nov. 13, 2013, Cesco-Cancian.
Abarghaz et al. "Regioelective Alkylation of the Exocyclic Nitrogen of Heterocyclic Amidines via the Mitsunobu Reaction" Tetrahedron Letters, 1995 vol. 36(36) pp. 6463-6466.
English, et al., Journal of the American Chemical Society, 1946, 68, 1039-1049.
Brown, et al.,Journal of the Chemical Society [Section C], Organic, 1967, (19), 1928-1933.
Siegel et al, "Rapid Parallel Synthesis Applied to the Optimization of a Series of Potent Nonpeptide Neuropeptide Y-1 Receptor Antagonists", Tetrahedron (1999) 55:11619-11639.
Song et al, "Synthesis of Cyclic Prodrugs of Aggrastat and Its Analogue with a Modified Phenylpropionic Acid Linker", Organic Letters (2002) 4(4):549-552.
Shultz, et al. "New Catalysts for the Oxidation of Sulfides to Sulfones with Hydrogen Peroxide" J. Org. Chem., 1963, 28, 1140.
Angel Alberola, et al., "Based-Induced Ring Cleavage of 4-Functionalized 3-Unsubstituted Isoxazoles. Synthesis of 2-Aminopyrimidines and Pyrimidine-2(3H)-Thiones", National Taiwan University Library, vol. 25, 1987, pp. 393-397.
Versha Vinay Kumar, et al, "Design, Synthesis and Biological Evaluation of 1,3-Diaminopropanes: A New Class of Polyamine Analogs as Leishmanicidal Agents", Bioorganic & Medicinal Chemistry Letters, vol. 7, No. 6, 1997, pp. 675-680.
James H. Short, et al., "Sympathetic Nervous Blocking Agents. Derivatives of Guanidine and Related Compounds", Journal of Medicinal Chemistry, vol. 6, 1963, pp. 275-283.
Japanese Application No. 2011-516757, Office Action dated Jul. 9, 2013.

* cited by examiner

Primary Examiner — James O Wilson
Assistant Examiner — Ebenezer O Sackey

(57) ABSTRACT

The present invention is directed to processes for the preparation of substituted pyrimidine derivatives, useful as intermediates in the synthesis of histamine $H_4$ receptor modulators, and to intermediates in H4 modulator synthesis.

3 Claims, No Drawings

PROCESS FOR THE PREPARATION OF SUBSTITUTED PYRIMIDINE DERIVATIVES

This application is a divisional application of U.S. patent application Ser. No. 13/844,227, filed on Mar. 15, 2013, which is a divisional application of U.S. patent application Ser. No. 13/663,233, filed on Oct. 29, 2012, which is a divisional application of U.S. patent application Ser. No. 12/459,229, filed on Jun. 29, 2009, now U.S. Pat. No. 8,309,720, which claims the benefit of U.S. Provisional Application 61/076,752, filed on Jun. 30, 2008, all of which are incorporated by reference herein in their entirety.

FIELD OF THE INVENTION

The present invention is directed to novel processes for the preparation of substituted pyrimidine derivatives, useful as intermediates in the synthesis of histamine $H_4$ receptor modulators, and to novel intermediates in $H_4$ modulator synthesis.

SUMMARY OF THE INVENTION

The present invention is directed to a process for the preparation of compounds of formula (I)

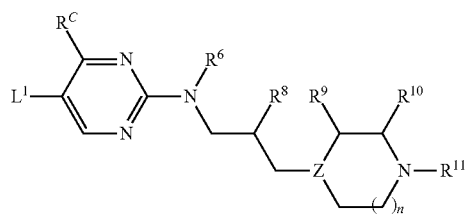

wherein $L^1$ is CN;

$R^c$ is selected from the group consisting of H, methyl, ethyl, propyl, isopropyl, —$CF_3$, cyclopropyl, and cyclobutyl;

$R^6$ is hydrogen;

$R^8$ is selected from the group consisting of hydrogen and $C_{1-4}$alkyl;

Z is selected from the group consisting of N and CH;

n is 1 or 2;

$R^9$, $R^{10}$ and $R^{11}$ are each independently selected from the group consisting of hydrogen and $C_{1-4}$alkyl;

and pharmaceutically acceptable salts thereof; comprising

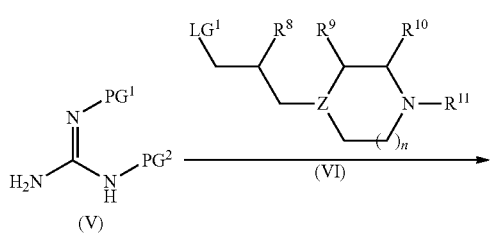

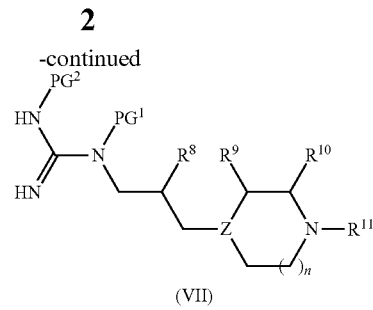

reacting a compound of formula (V) wherein $PG^1$ and $PG^2$ are each independently a nitrogen protecting group, with a compound of formula (VI), wherein $LG^1$ is a leaving group, in a first organic solvent; and when $LG^1$ is —OH, in the presence of a coupling agent system; to yield the corresponding compound of formula (VII);

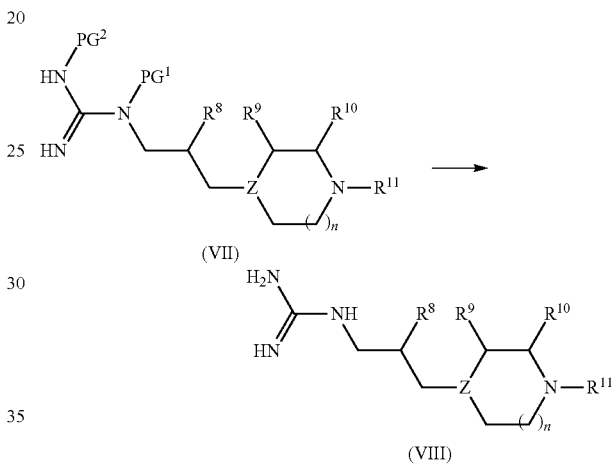

de-protecting the compound of formula (VII), to yield the corresponding compound of formula (VIII); and

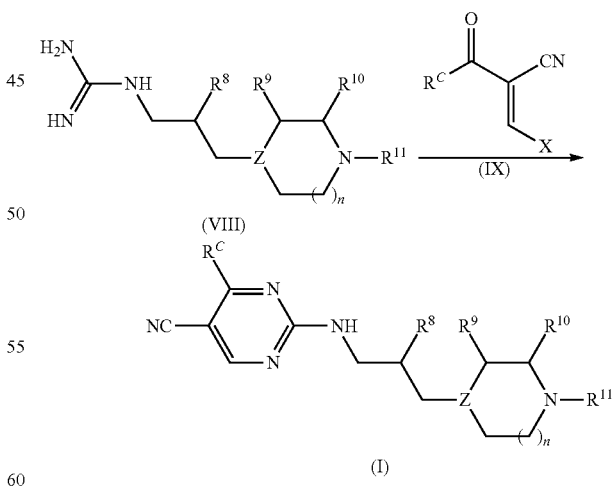

reacting, in a second organic solvent, the compound of formula (VIII) with a compound of formula (IX), to yield the corresponding compound of formula (I), wherein X is selected from the group consisting of —$N(R^{20})_2$ and —$OR^{21}$; wherein the $R^{20}$ groups may be the same or different from each other, so such each $R^{20}$ is independently selected from the other R²⁰ and such selection is made from the group consisting of $C_{1-4}$alkyl substituents (concisely put, each R²⁰ is independently selected from the group consisting of $C_{1-4}$alkyl); alternatively the two R²⁰ groups are taken together with the nitrogen atom to which they are bound to form a saturated ring structure selected from the group consisting of piperidinyl, pyrrolidinyl and morpholinyl; and wherein R²¹ is selected from the group consisting of $C_{1-4}$alkyl and benzyl.

In an embodiment, the present invention is directed to a process for the preparation of a compound of formula (I-S)

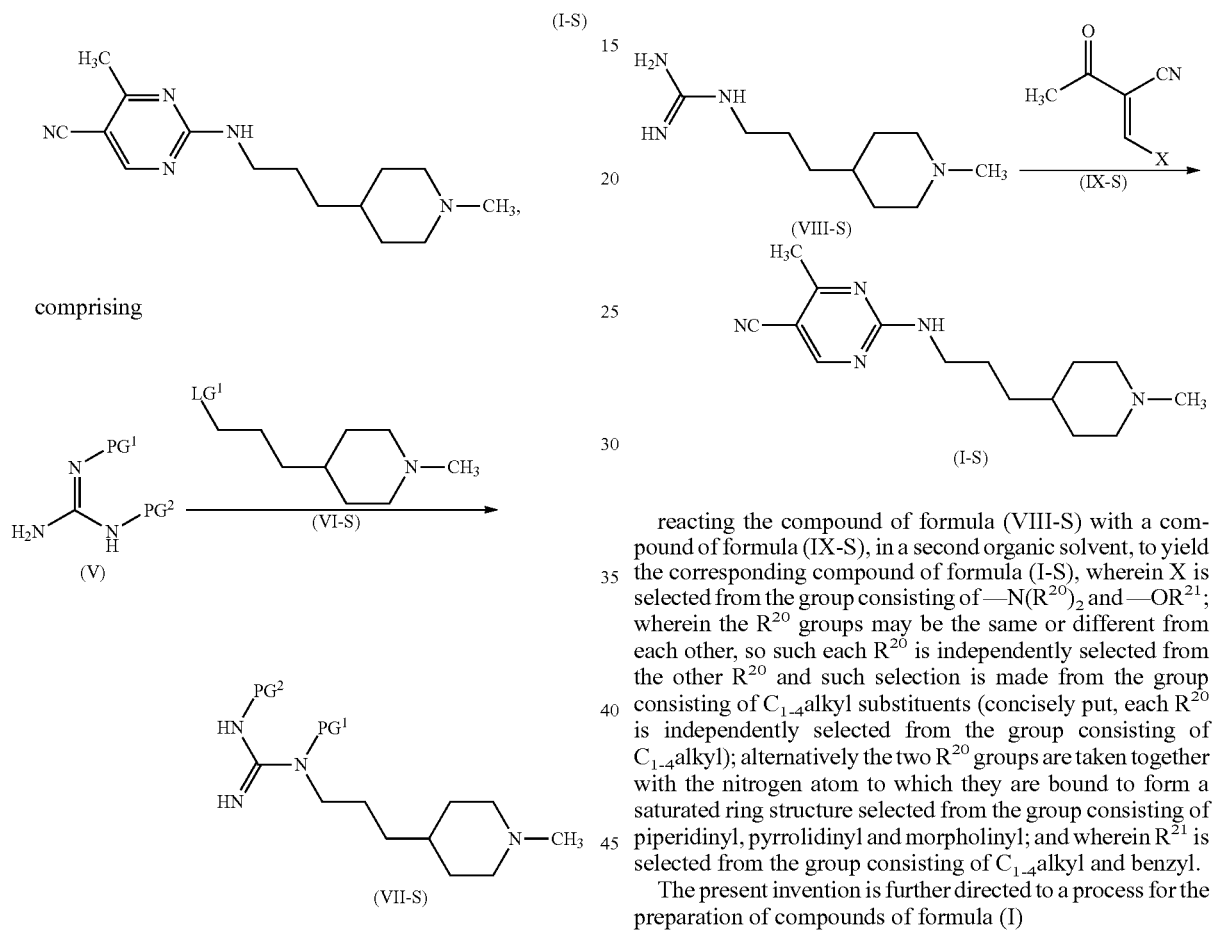

comprising

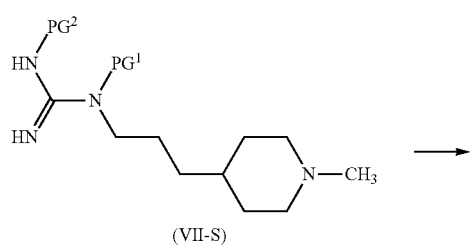

reacting a compound of formula (V) wherein PG¹ and PG² are each independently a nitrogen protecting group, with a compound of formula (VI-S), wherein LG¹ is a leaving group, in a first organic solvent; and when LG¹ is —OH, in the presence of a coupling agent system; to yield the corresponding compound of formula (VII-S);

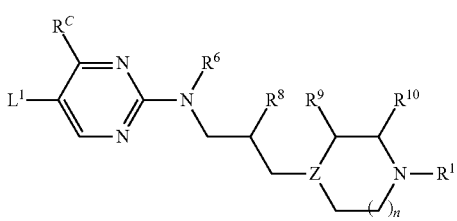

de-protecting the compound of formula (VII-S), to yield the corresponding compound of formula (VIII-S); and reacting the compound of formula (VIII-S) with a compound of formula (IX-S), in a second organic solvent, to yield the corresponding compound of formula (I-S), wherein X is selected from the group consisting of —N(R²⁰)₂ and —OR²¹; wherein the R²⁰ groups may be the same or different from each other, so such each R²⁰ is independently selected from the other R²⁰ and such selection is made from the group consisting of $C_{1-4}$alkyl substituents (concisely put, each R²⁰ is independently selected from the group consisting of $C_{1-4}$alkyl); alternatively the two R²⁰ groups are taken together with the nitrogen atom to which they are bound to form a saturated ring structure selected from the group consisting of piperidinyl, pyrrolidinyl and morpholinyl; and wherein R²¹ is selected from the group consisting of $C_{1-4}$alkyl and benzyl.

The present invention is further directed to a process for the preparation of compounds of formula (I)

wherein
L¹ is CN;
R^c is selected from the group consisting of H, methyl, ethyl, propyl, isopropyl, —CF₃, cyclopropyl, and cyclobutyl;
R⁶ is hydrogen;
R⁸ is selected from the group consisting of hydrogen and $C_{1-4}$alkyl;

Z is selected from the group consisting of N and CH;

n is 1 or 2;

$R^9$, $R^{10}$ and $R^{11}$ are each independently selected from the group consisting of hydrogen and $C_{1-4}$alkyl;

and pharmaceutically acceptable salts thereof; comprising

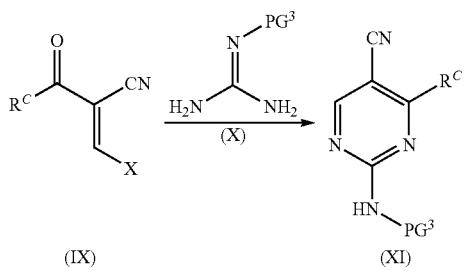

reacting a compound of formula (IX) wherein X is selected from the group consisting of —$N(R^{20})_2$ and —$OR^{21}$; wherein the $R^{20}$ groups may be the same or different from each other, so such each $R^{20}$ is independently selected from the other $R^{20}$ and such selection is made from the group consisting of $C_{1-4}$alkyl substituents (concisely put, each $R^{20}$ is independently selected from the group consisting of $C_{1-4}$alkyl); alternatively the two $R^{20}$ groups are taken together with the nitrogen atom to which they are bound to form a saturated ring structure selected from the group consisting of piperidinyl, pyrrolidinyl and morpholinyl; and wherein $R^{21}$ is selected from the group consisting of $C_{1-4}$alkyl and benzyl; with a compound of formula (X), wherein $PG^3$ is a nitrogen protecting group, in a first organic solvent, to yield the corresponding compound of formula (XI);

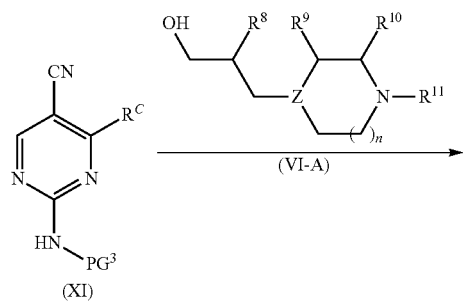

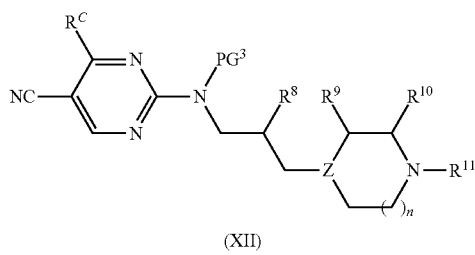

reacting the compound of formula (XI) with a compound of formula (VI-A), in the presence of a coupling agent system, in a second organic solvent, to yield the corresponding compound of formula (XII); and

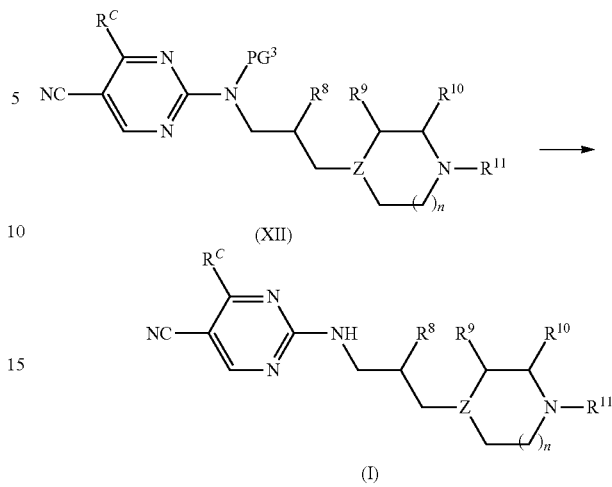

de-protecting the compound of formula (XII), to yield the corresponding compound of formula (I).

In an embodiment, the present invention is directed to a process for the preparation of a compound of formula (I-S)

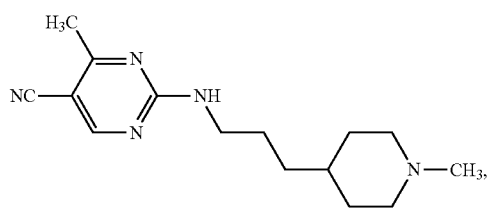

comprising

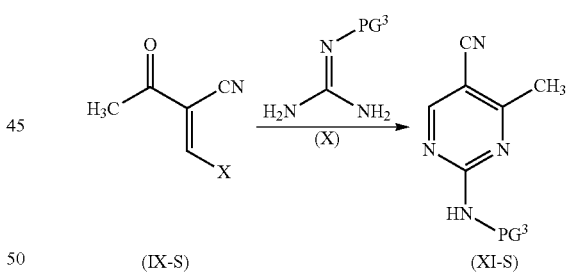

reacting a compound of formula (IX-S) wherein X is selected from the group consisting of —$N(R^{20})_2$ and —$OR^{21}$; wherein the $R^{20}$ groups may be the same or different from each other, so such each $R^{20}$ is independently selected from the other $R^{20}$ and such selection is made from the group consisting of $C_{1-4}$alkyl substituents (concisely put, each $R^{20}$ is independently selected from the group consisting of $C_{1-4}$alkyl, an abridged form of assignment expression used herein whether given in a more extended form or not, unless otherwise specified); alternatively the two $R^{20}$ groups are taken together with the nitrogen atom to which they are bound to form a saturated ring structure selected from the group consisting of piperidinyl, pyrrolidinyl and morpholinyl; and wherein $R^{21}$ is selected from the group consisting of $C_{1-4}$alkyl and benzyl; with a compound of formula (X), wherein $PG^3$ is a nitrogen protecting group, in a first organic solvent, to yield the corresponding compound of formula (XI-S);

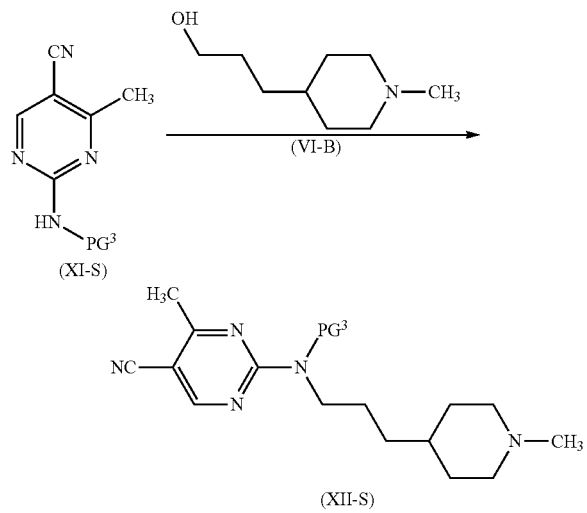

reacting the compound of formula (XI-S) with a compound of formula (VI-B), in the presence of a coupling agent system, in a second organic solvent, to yield the corresponding compound of formula (XII-S); and

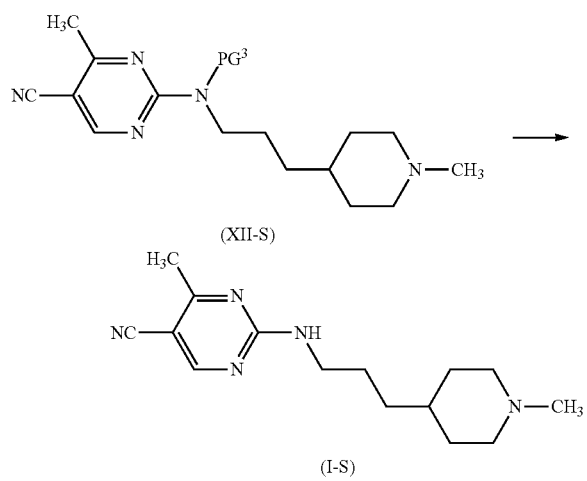

de-protecting the compound of formula (XII-S), to yield the corresponding compound of formula (I-S).

The present invention is further directed to a product prepared according to any of the processes described herein.

The present invention is further directed to compounds of formula (I)

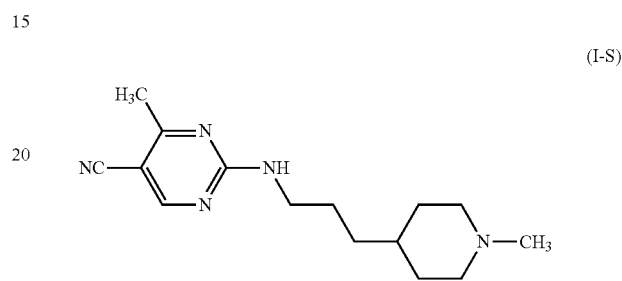

wherein
$L^1$ is CN;
$R^c$ is selected from the group consisting of H, methyl, ethyl, propyl, isopropyl, —$CF_3$, cyclopropyl, and cyclobutyl;
$R^6$ is hydrogen;
$R^8$ is selected from the group consisting of hydrogen and $C_{1-4}$alkyl;
Z is selected from the group consisting of N and CH;
n is 1 or 2;
$R^9$, $R^{10}$ and $R^{11}$ are each independently selected from the group consisting of hydrogen and $C_{1-4}$alkyl;
and pharmaceutically acceptable salts thereof. In an embodiment, present invention is directed to a compound of formula (I-S)

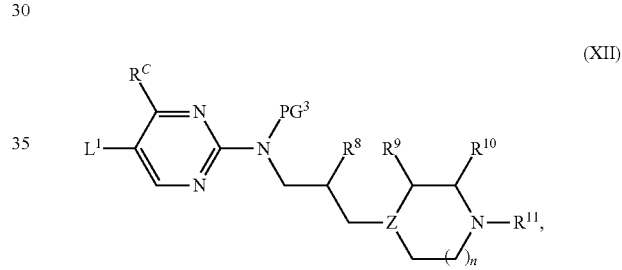

and pharmaceutically acceptable salts thereof.

The present invention is further directed to compounds of formula (XII)

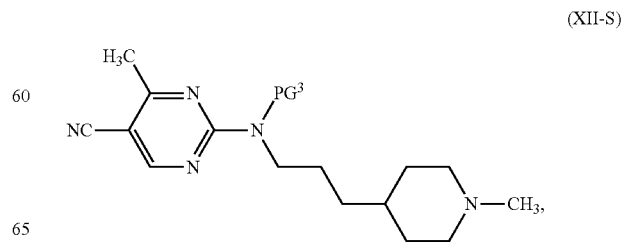

wherein
$PG^3$ is a nitrogen protecting group;
$L^1$ is CN;
$R^c$ is selected from the group consisting of H, methyl, ethyl, propyl, isopropyl, —$CF_3$, cyclopropyl, and cyclobutyl;
$R^8$ is selected from the group consisting of hydrogen and $C_{1-4}$alkyl;
Z is selected from the group consisting of N and CH;
n is 1 or 2;
$R^9$, $R^{10}$ and $R^{11}$ are each independently selected from the group consisting of hydrogen and $C_{1-4}$alkyl;
and pharmaceutically acceptable salts thereof. In an embodiment, present invention is directed to a compound of formula (XII-S)

and pharmaceutically acceptable salts thereof, wherein PG³ is defined as for compounds of formula (XII).

The present invention is further directed to compounds of formula (XI)

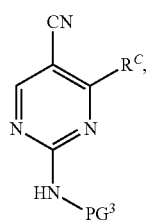

(XI)

wherein PG³ is a nitrogen protecting group; R^c is selected from the group consisting of H, methyl, ethyl, propyl, isopropyl, —CF₃, cyclopropyl, and cyclobutyl; and pharmaceutically acceptable salts thereof. In an embodiment, the present invention is directed to a compound of formula (XI-S)

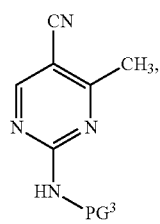

(XI-S)

and pharmaceutically acceptable salts thereof, wherein PG³ is defined as for compounds of formula (XI). In another embodiment, the present invention is directed to a compound of formula (XI-S), wherein PG³ is selected from the group consisting of —C(O)OCH₂CH₃ and —C(O)OC(CH₃)₃, and pharmaceutically acceptable salts thereof.

The present invention is further directed to compounds of formula (XX)

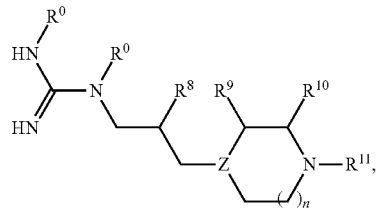

(XX)

wherein
R⁰ is hydrogen or a nitrogen protecting group; and wherein the two R⁰ groups are the same;
R⁸ is selected from the group consisting of hydrogen and C₁₋₄alkyl;
Z is selected from the group consisting of N and CH;
n is 1 or 2;
R⁹, R¹⁰ and R¹¹ are each independently selected from the group consisting of hydrogen and C₁₋₄alkyl;
provided that when each of R⁸, R⁹ and R¹⁰ is hydrogen, n is 1 or 2, and R¹¹ is methyl, then R⁰ is a nitrogen protecting group other than —C(O)O—CH₃; (i.e. R⁰ is not hydrogen or —C(O)OCH₃);

and pharmaceutically acceptable salts thereof. The compounds of formula (XX) correspond to the compounds of formula (VII) when R⁰ is a nitrogen protecting group; and to the compounds of formula (VIII), when R⁰ is hydrogen; and are therefore useful as intermediates in the synthesis of the compounds of formula (I). In an embodiment, the present invention is directed to compounds of formula (XX-S)

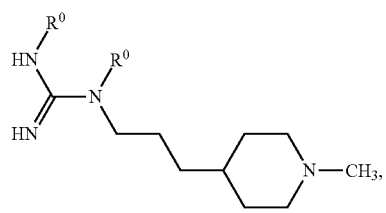

(XX-S)

and pharmaceutically acceptable salts thereof, wherein R⁰ is defined as for compounds of formula (XX). In another embodiment of the present invention, R⁰ is selected from the group consisting of hydrogen or a nitrogen protecting group wherein the nitrogen protecting group is selected from the group consisting of CBz, Boc, Troc and Alloc. In another embodiment of the present invention, R⁰ is selected from the group consisting of hydrogen and CBz.

DETAILED DESCRIPTION OF THE INVENTION

The present invention is directed to compounds of formula (I)

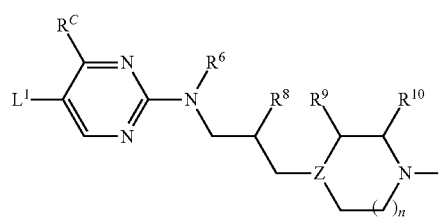

(I)

wherein L¹, R^C, R⁶, R⁸, R⁹, R¹⁰, R¹¹, Z and n are as herein defined; and further directed to processes for the preparation of the compounds of formula (I). The compounds of formula (I) of the present invention are useful as intermediates in the synthesis of histamine H₄ receptor modulators, for example benzoimidazol-2-yl pyrimidines as described in US Patent Publication US20070244126A1, published on Oct. 18, 2007. The present invention is further directed to intermediates in the synthesis of the compounds of formula (I), more particularly to compounds of formula (VII), compounds of formula (VIII) and compounds of formula (XI), as herein defined.

In an embodiment of the present invention, Z is CH. In another embodiment of the present invention, n is 1. In yet another embodiment of the present invention, R⁸, R⁹ and R¹⁰ are each hydrogen. In yet another embodiment of the present invention, R¹¹ is methyl. In yet another embodiment of the present invention, the compound of formula (I) is the compound of formula (I-S)

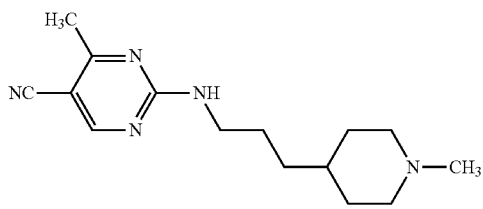

(I-S)

or a pharmaceutically acceptable salt thereof. One of ordinary skill in the art will recognize that the compound of formula (IS) corresponds to a compound of formula (I) wherein $R^8$ is hydrogen, $R^9$ is hydrogen, $R^{10}$ is hydrogen, Z is CH, n is 1, and $R^{11}$ is methyl.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol "I"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

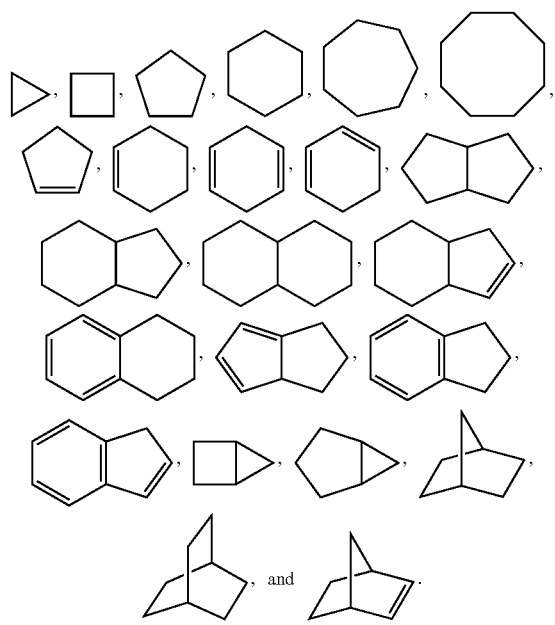

When a particular group is "substituted" (e.g., cycloalkyl, aryl, heteroaryl, heterocycloalkyl, etc.), that group may have one or more substituents, for example, from one to five substituents, or from one to three substituents, or one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. In an embodiment, wherein the compound is present as an enantiomer, the enantiomer is present at an enantiomeric excess of greater than or equal to about 80%, for example, at an enantiomeric excess of greater than or equal to about 90%. In another example, the compound is present at an enantiomeric excess of greater than or equal to about 95%. In another example, the compound is present at an enantiomeric excess of greater than or equal to about 98%. In yet another example, the compound is present at an enantiomeric excess of greater than or equal to about 99%. Similarly, wherein the compound is present as a diastereomer, the diastereomer is present at an diastereomeric excess of greater than or equal to about 80%, for example, at an diastereomeric excess of greater than or equal to about 90%. In another example, the compound is present at an diastereomeric excess of greater than or equal to about 95%. In another example, the compound is present at an diastereomeric excess of greater than or equal to about 98%. In yet another example, the compound is present at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

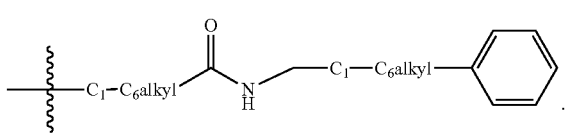

Abbreviations used in the specification, particularly the Schemes and Examples, are as follows
$Ac_2O$=Acetic anhydride
AcOH or HOAc=Acetic acid
ADDP=1,1'-(Azodicarbonyl)dipiperidine
Alloc=Allyloxycarbonyl
BOC or Boc=t-Butoxycarbonyl
$BOC_2O$=Boc anhydride
$Bu_3P$ or $PBu_3$=Tri-n-butylphosphine
CBz=Carbobenzyloxy (or Benzyloxycarbonyl)
DBU=1,8-Diazabicyclo[5.4.0]undec-7-ene DEAD=Diethylazodicarboxylate
DIAD=Diisopropylazodicarboxylate
DIPEA or DIEA=Diisopropylethylamine
DMF=N,N-Dimethylformamide
DMF.DMA=Dimethylformamide dimethylacetal
DMSO=Dimethylsulfoxide
EtOAc=Ethyl acetate
EtOH=Ethanol
HPLC=High Pressure Liquid Chromatography
IPA=Isopropyl alcohol
MeOH=Methanol
2-Me-THF=2-Methyl-tetrahydrofuran
Mesylate=Methyl sulfonate (i.e. O—$SO_2$—$CH_3$)
MTBE=Methyl-t-butyl ether
NaOAc=Sodium acetate
NaOEt=Sodium Ethoxide
Pd—C=Palladium on Carbon Catalyst
$PPh_3$ or TPP=Triphenylphosphine
Rh/C=Rhodium on Carbon
TEA=Triethylamine
THF=Tetrahydrofuran
Troc=2,2,2-Trichloroethoxycarbonyl As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One of ordinary skill in the art will recognize that, where not otherwise specified, the reaction step(s) is(are) performed under suitable conditions, according to known methods, to provide the desired product. One of ordinary skill in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same as or different from the organic or inorganic base of the second step. Further, one of ordinary skill in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Examples of suitable solvents, bases, reaction temperatures, and other reaction parameters and components are provided in the detailed descriptions which follow herein. One of ordinary skill in the art will recognize that the listing of said examples is provided for illustrative purposes, and that it is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene and acetone.

As used herein, unless otherwise noted, the term "leaving group" shall mean a charged or uncharged atom or group which departs during a substitution or displacement reaction. Although leaving groups in such reactions are well known and within the knowledge of those of ordinary skill in the art, some illustrative suitable examples are given here, and they include, but are not limited to, OH, Br, Cl, I, mesylate, tosylate, cyano and triflate.

As used herein, unless otherwise noted, the term "nitrogen protecting group" shall mean a group which may be attached to a nitrogen atom to protect said nitrogen atom from participating in a reaction and which may be readily removed following the reaction. Illustrative suitable nitrogen protecting groups include, but are not limited to, carbamates (which are groups that contain a moiety —C(O)O—R, wherein R is for example methyl, ethyl, t-butyl, benzyl, phenylethyl, $CH_2$=CH—$CH_2$— and 2,2,2-trichloroethyl); amides (which are groups that contain a moiety —C(O)—R', wherein R' is for example methyl, phenyl, trifluoromethyl and t-butyl (pivalol)); N-sulfonyl derivatives (which are groups that contain a moiety —$SO_2$—R", wherein R" is for example methyl, tolyl, phenyl, trifluoromethyl, 2,2,5,7,8-pentamethylchroman-6-yl- and 2,3,6-trimethyl-4-methoxybenzene). Choice of protecting groups is within the ordinary skill in the art, and an ample variety of such groups, how to obtain them and their behavior is given in standard reference materials, such as P. G. M. Wuts & T. W. Greene, Protective Groups in Organic Synthesis, John Wiley & Sons, 2007, and Protective Groups in Organic Chemistry, ed. J. F. W. McOmie, Plenum Press, 1973.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and P. G. M. Wuts & T. W. Greene *Protective Groups in Organic Synthesis*, John Wiley & Sons, 2007. The protecting groups may be removed at a convenient subsequent stage using methods known from the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Reference to a chemical entity herein by naming one of its forms stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. In another example, a zwitterionic compound is encompassed herein by referring to a compound that is known to form a zwitterions, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Inerest (ChEBI) dictionary of molecular entities. (See, for example its on line version at http://www.ebi.ac.uk/chebi/init.do). As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention, where applicable, are given explicitly herein. They are, however, part of the embodiments of this invention when compounds referred to herein can form such zwitterions. No further examples in this regard are provided herein because the interactions and transformations in a given medium that lead to the various forms of a given compound are known by any one of ordinary skill in the art.

The present invention is directed to a process for the preparation of compounds of formula (I) as outlined in Scheme 1, below.

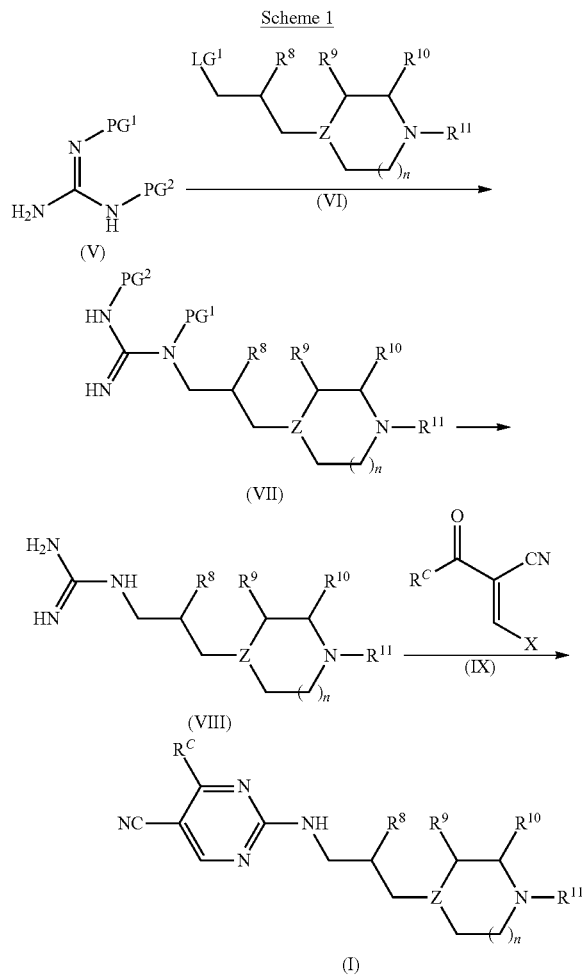

Accordingly, a suitably substituted compound of formula (V), wherein PG$^1$ and PG$^2$ are each independently a suitably selected nitrogen protecting group such as CBz, BOC, Troc, or Alloc, for example, PG$^1$ and PG$^2$ are each CBz, a known compound or compound prepared by known methods, is reacted with a suitably substituted compound of formula (VI), wherein LG$^1$ is a suitably selected leaving group such as OH, Cl, Br, I or mesylate, for example OH; wherein the compound of formula (VI) is present in, for example, an amount in the range of from about 1.0 to about 1.2 molar equivalents, for example about 1.01 molar equivalents; and when LG$^1$ is OH, in the presence of a suitably selected coupling agent system such as DIAD and PPh$_3$, DEAD and PPh$_3$, or ADDP and PBu$_3$, for example DIAD and PPh$_3$; wherein the PPh$_3$ of the coupling agent system is optionally present on a solid support; and wherein the coupling agent system is present in, for example, an amount in the range of from about 1.0 to about 1.4 molar equivalents, for example 1.2 molar equivalents; and in a first organic solvent or mixture of organic solvents such as THF, 2-methyl-THF, toluene, acetonitrile, DMF or ethyl acetate, for example in 2-methyl-THF; at a temperature in the range of from about −10° C. to about room temperature, for example at about 5° C.; to yield the corresponding compound of formula (VII).

In an embodiment of the present invention, PG$^1$ and PG$^2$ are the same and are a suitably selected nitrogen protecting group such as CBz or BOC. In another embodiment of the present invention, PG$^1$ and PG$^2$ are the same nitrogen protecting group and are each CBz.

The compound of formula (VII) is de-protected according to known methods, to yield the corresponding compound of formula (VIII), as a free base or as its corresponding salt form (for example as its corresponding HCl salt). For example, wherein PG$^1$ and PG$^2$ are each CBz, the compound of formula (VII) is de-protected by reacting with hydrogen gas at a pressure of about 60 psi, in the presence of a catalyst such as Pd/C, in a solvent such as ethanol.

The compound of formula (VIII), as a free base or as its corresponding salt form (for example as its corresponding HCl salt), is reacted with a suitably substituted compound of formula (IX), wherein X is selected from the group consisting of —N(R$^{20}$)$_2$ and —OR$^{21}$; wherein each R$^{20}$ is independently selected from the group consisting of C$_{1-4}$alkyl; alternatively the two R$^{20}$ groups are taken together with the nitrogen atom to which they are bound to form a saturated ring structure selected from the group consisting of piperidinyl, pyrrolidinyl and morpholinyl; and wherein R$^{21}$ is selected from the group consisting of C$_{1-4}$alkyl and benzyl, for example, wherein X is —N(CH$_3$)$_2$; a known compound or compound prepared by known methods, wherein the compound of formula (IX) is present in, for example, an amount in the range of from about 1.0 to about 2.0 molar equivalents, for example, about 1.5 molar equivalents; optionally in the presence of a base such as TEA, DIPEA, DBU, sodium t-butoxide, potassium t-butoxide, sodium methoxide, sodium ethoxide, K$_2$CO$_3$, Na$_2$CO$_3$, Cs$_2$CO$_3$ or NaHCO$_3$, for example, an inorganic base such as powdered K$_2$CO$_3$, wherein the base is present in an amount in the range of from about 0 to about 2 molar equivalents, for example, about 2 molar equivalents; in a second organic solvent such as ethanol, isopropanol, ethyl acetate or acetonitrile, for example in ethanol; at a temperature in the range of from about room temperature to about 80° C., for example at about solvent reflux temperature; to yield the corresponding compound of formula (I).

One of ordinary skill in the art will recognize that compounds of formula (VIII) may alternatively be prepared by reacting a suitably substituted compound of formula (VI) with a tri-protected compound of formula (V), as described in more detail in Examples 26 through 28, which follow herein. One of ordinary skill in the art will further recognize that compounds of formula (VII) may alternatively be prepared by reacting a compound of formula (L)

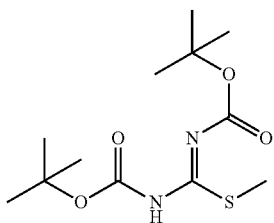

(L)

as described in more detail in Examples 29 through 30 and further in Example 31, which follow herein.

In an embodiment, the present invention is directed to a process for the preparation of a compound of formula (I-S), as outlined in Scheme 2 below.

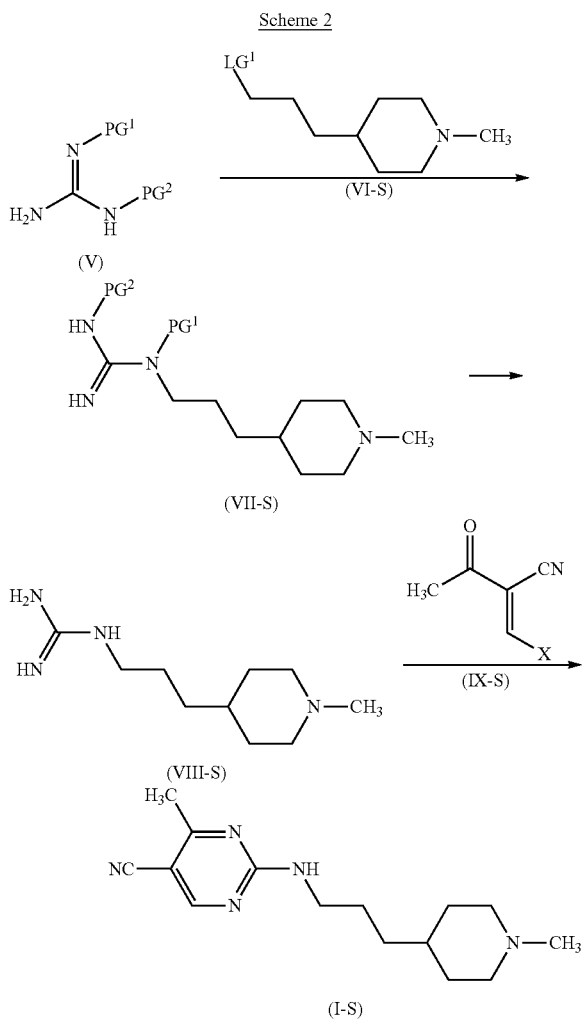

Accordingly, a suitably substituted compound of formula (V), wherein $PG^1$ and $PG^2$ are each independently a suitably selected nitrogen protecting group such as CBz, BOC, Troc, or Alloc, for example, $PG^1$ and $PG^2$ are each CBz, a known compound or compound prepared by known methods, is reacted with a suitably substituted compound of formula (VI), wherein $LG^1$ is a suitably selected leaving group such as OH, Cl, Br, I or mesylate, for example OH; wherein the compound of formula (VI-S) is present in, for example, an amount in the range of from about 1.0 to about 1.2 molar equivalents, for example about 1.01 molar equivalents; and when $LG^1$ is OH, in the presence of a suitably selected coupling agent system such as DIAD and $PPh_3$, DEAD and $PPh_3$, or ADDP and $PBu_3$, for example DIAD and $PPh_3$; wherein the $PPh_3$ of the coupling agent system is optionally present on a solid support; and wherein the coupling agent system is present in, for example, an amount in the range of from about 1.0 to about 1.4 molar equivalents, for example 1.2 molar equivalents; and in a first organic solvent or mixture of organic solvents such as THF, 2-methyl-THF, toluene, acetonitrile, DMF or ethyl acetate, for example in 2-methyl-THF; at a temperature in the range of from about −10° C. to about room temperature, for example at about 5° C.; to yield the corresponding compound of formula (VII-S).

In an embodiment of the present invention, $PG^1$ and $PG^2$ are the same and are a suitably selected nitrogen protecting group such as CBz or BOC. In another embodiment of the present invention, $PG^1$ and $PG^2$ are the same nitrogen protecting group and are each CBz.

The compound of formula (VII-S) is de-protected according to known methods, to yield the corresponding compound of formula (VIII-S), as a free base or as its corresponding salt form (for example as its corresponding HCl salt). For example, wherein $PG^1$ is CBz, the compound of formula (VII-S) is de-protected by reacting with hydrogen gas at a pressure of about 60 psi, in the presence of a catalyst such as Pd/C, in a solvent such as ethanol.

The compound of formula (VIII-S), as a free base or as its corresponding salt form (for example as its corresponding HCl salt), is reacted with a suitably substituted compound of formula (IX-S), wherein X is selected from the group consisting of —$N(R^{20})_2$ and —$OR^{21}$; wherein each $R^{20}$ is independently selected from the group consisting of $C_{1-4}$alkyl; alternatively the two $R^{20}$ groups are taken together with the nitrogen atom to which they are bound to form a saturated ring structure selected from the group consisting of piperidinyl, pyrrolidinyl and morpholinyl; and wherein $R^{21}$ is selected from the group consisting of $C_{1-4}$alkyl and benzyl, for example, wherein X is —$N(CH_3)_2$; a known compound or compound prepared by known methods, wherein the compound of formula (IX-S) is present in, for example, an amount in the range of from about 1.0 to about 2.0 molar equivalents, for example, about 1.5 molar equivalents; optionally in the presence of a base such as TEA, DIPEA, DBU, sodium t-butoxide, potassium t-butoxide, sodium ethoxide, sodium methoxide, $K_2CO_3$, $Na_2CO_3$, $Cs_2CO_3$ or $NaHCO_3$, for example, an inorganic base such as powdered $K_2CO_3$, wherein the base is present in an amount in the range of from about 0 to about 2 molar equivalents, for example, about 2 molar equivalents; in a second organic solvent such as ethanol, isopropanol, ethyl acetate or acetonitrile, for example in ethanol; at a temperature in the range of from about room temperature to about 80° C., for example at about solvent reflux temperature; to yield the corresponding compound of formula (I-S).

The compound of formula (V) may be prepared by protecting guanidine according to known methods. For example, the compound of formula (V), wherein $PG^1$ is CBz may be prepared by reacting guanidine with Cbz-Cl, a known compound, in the presence of a base such as NaOH, in a mixture of water and THF. The preparation of a compound of formula (V) wherein $PG^1$ is CBz is outlined in more detail in Example 13 which follows herein.

The compound of formula (VI-S) may be prepared by for example, reacting 3-pyrid-4-yl-propan-1-ol, a known compound, with hydrogen gas at a pressure of about 300 psi, in the presence of a catalyst such as Pd/C, in a suitably selected solvent or mixture of solvents such as water or a mixture of about 3:1 methanol:acetic acid, at a temperature in the range of about 20-50° C. to yield the corresponding 3-piperidin-4-yl-propan-1-ol. The 3-piperidin-4-yl-propan-1-ol is then reacted with formaldehyde, a known compound, in the presence of hydrogen gas at about 85 psi and a catalyst such as Pd/C, in a suitably selected solvent or mixture of solvents such as water or a mixture of about 3:1 methanol:acetic acid, at a temperature of about 0-45° C. The preparation of a compound of formula (VI-S) in water, is outlined in more detail in Example 2 which follows herein.

The compound of formula (IX-S) may be prepared by for example, reacting 3-amino-but-2-enenitrile, a known compound, with an acid such as 3M HCl, in an organic solvent such as ethyl acetate, to yield 3-oxo-butyronitrile, which is further reacted with DMF.DMA, in an organic solvent such as ethyl acetate, at about room temperature. The preparation of a compound of formula (IX-S) is outlined in more detail in Example 1 which follows herein.

The present invention is directed to a process for the preparation of compounds of formula (I) as outlined in Scheme 3, below.

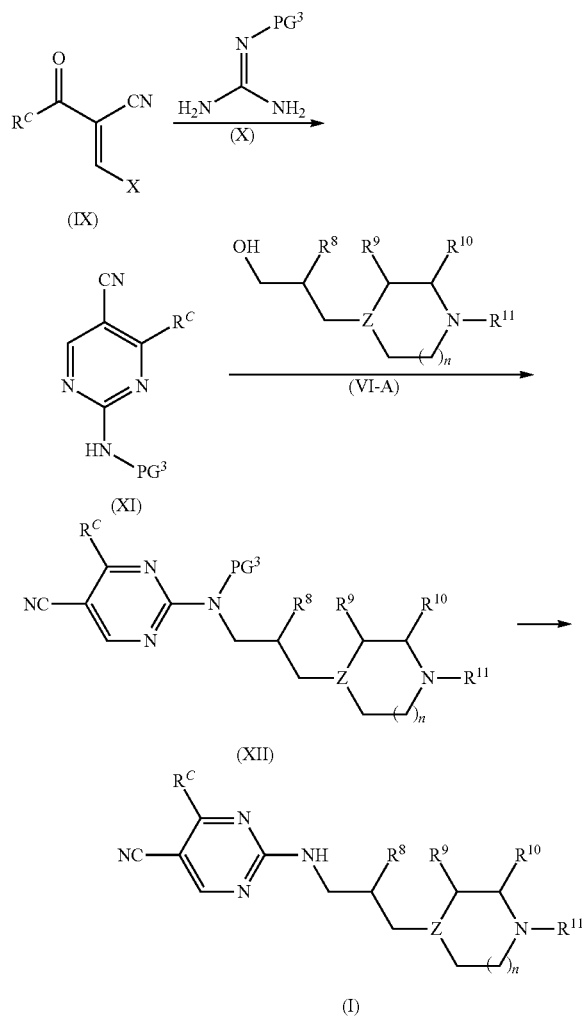

Scheme 3

Accordingly, a compound of formula (IX), wherein X is selected from the group consisting of $-N(R^{20})_2$ and $-OR^{21}$;

wherein each $R^{20}$ is independently selected from the group consisting of $C_{1-4}$alkyl (preferably dimethylamino); alternatively the two $R^{20}$ groups are taken together with the nitrogen atom to which they are bound to form a saturated ring structure selected from the group consisting of piperidinyl, pyrrolidinyl and morpholinyl; and wherein $R^{21}$ is selected from the group consisting of $C_{1-4}$alkyl and benzyl, for example, wherein X is $-N(CH_3)_2$; a known compound or compound prepared by known methods, is reacted with a suitably substituted compound of formula (X), wherein $PG^3$ is a suitably selected nitrogen protecting group such as $-C(O)CH_3$, $-C(O)OCH_2CH_3$, $-C(O)O$-t-butyl (Boc), $-CHO$, $-C(O)OCH_3$, $-C(O)O-CH_2$-phenyl, $-C(O)$-phenyl, $-C(O)OCH_2CCl_3$, $-C(O)$-(4-nitrophenyl), $-C(O)CCl_3$, $-C(O)CF_3$, $-SO_2CH_3$, $-SO_2$-phenyl, $-SO_2$-(4-nitrophenyl), or $-SO_2CF_3$, for example $-C(O)CH_3$, $C(O)OCH_2CH_3$ or $-C(O)O$-t-butyl (Boc), a known compound or compound prepared by known methods; wherein the compound of formula (IX) is present in an amount in the range of from about 1.0 to about 4.0 molar equivalents, for example about 1.5 molar equivalents; in a first organic solvent such as ethanol, isopropanol, acetonitrile or 2-methyl-THF, for example in 2-methyl-THF; at a temperature in the range of from about room temperature to about 80° C., for example at about 80° C.; to yield the corresponding compound of formula (XI).

In an embodiment of the present invention, $PG^3$ is selected from the group consisting of $-C(O)CH_3$, $-C(O)OCH_2CH_3$, $-C(O)O$-t-butyl (Boc), $-CHO$, $-C(O)OCH_3$, $-C(O)O-CH_2$-phenyl, $-C(O)$-phenyl, $-C(O)OCH_2CCl_3$, $-C(O)$-(4-nitrophenyl), $-C(O)CCl_3$, $-C(O)CF_3$, $-SO_2CH_3$, $-SO_2$-phenyl, $-SO_2$-(4-nitrophenyl) and $-SO_2CF_3$. In another embodiment of the present invention, $PG^3$ is selected from the group consisting of $-C(O)CH_3$, $-C(O)OCH_2CH_3$, $-C(O)O$-t-butyl (Boc), $-CHO$, $-C(O)OCH_3$, $-C(O)O-CH_2$-phenyl and $-C(O)$-phenyl. In another embodiment of the present invention, $PG^3$ is selected from the group consisting of $-C(O)CH_3$, $-C(O)OCH_2CH_3$ and $-C(O)O$-t-butyl (Boc). In another embodiment of the present invention, $PG^3$ is $-C(O)CH_3$.

In an embodiment of the present invention, $PG^3$ is a suitably selected nitrogen protecting group, wherein the pKa of the compound of formula (X) is less than about 13. In another embodiment of the present invention, $PG^3$ is a suitably selected nitrogen protecting group, wherein the pKa of the compound of formula (X) is in the range of about 13 to about 9, or any range therein. In an embodiment of the present invention, $PG^3$ is a suitably selected nitrogen protecting group, wherein the pKa of the compound of formula (X) is in the range of about 13 to about 11, or any range therein.

The compound of formula (XI) is reacted with a compound of formula (VI-A), a known compound or compound prepared by known methods; wherein the compound of formula (VI-A) is present in an amount in the range of from about 1.0 to about 3.0 molar equivalents, for example about 1.5 molar equivalents; in the presence of a suitably selected coupling agent system such as DIAD and $PPh_3$, DEAD and $PPh_3$, or ADDP and $PBu_3$, for example DIAD and $PPh_3$; wherein the $PPh_3$ of the coupling agent system is optionally present on a solid support; and wherein the coupling agent system is present in, for example, an amount in the range of from about 1.0 to about 2.0 molar equivalents, for example 1.2 molar equivalents; in a second organic solvent such as THF, 2-methyl-THF, toluene, acetonitrile, ethyl acetate or DMF, for example in 2-methyl-THF; at a temperature in the range of from about $-10°$ C. to about room temperature, for example at about 5° C.; to yield the corresponding compound of formula (XII).

The compound of formula (XII) is de-protected according to known methods, to yield the corresponding compound of formula (I). For example, wherein $PG^3$ is —C(O)O—C(CH$_3$)$_3$ (BOC), the compound of formula (XII-S) may be de-protected by reacting with a suitably selected acid such as HCl, and the like; alternatively, wherein $PG^3$ is —C(O)—CH$_3$ or —C(O)O—CH$_2$CH$_3$, the compound of formula (XII-S) may be de-protected by reacting with a suitably selected base such as NaOH, and the like. One skilled in the art will recognize that the compound of formula (XII) may be de-protected as a discrete or separate reaction step (as described for example in Example 7, Step B, which follows herein); or alternatively, in the work-up of the compound of formula (XII) (as described for example, in Examples 10 and 12, which follow herein).

In an embodiment, the present invention is directed to a process for the preparation of a compound of formula (I-S), as outlined in Scheme 4 below.

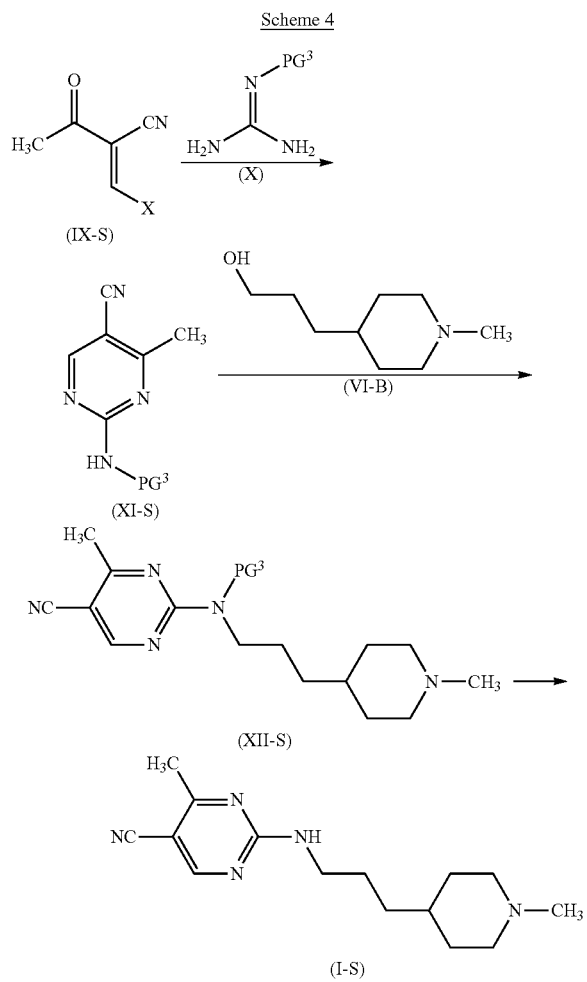

Accordingly, a compound of formula (IX-S), wherein X is selected from the group consisting of —N(R$^{20}$)$_2$ and —OR$^{21}$; wherein each R$^{20}$ is independently selected from the group consisting of C$_{1-4}$alkyl (preferably dimethylamino); alternatively the two R$^{20}$ groups are taken together with the nitrogen atom to which they are bound to form a saturated ring structure selected from the group consisting of piperidinyl, pyrrolidinyl and morpholinyl; and wherein R$^{21}$ is selected from the group consisting of C$_{1-4}$alkyl and benzyl, for example, wherein X is —N(CH$_3$)$_2$; a known compound or compound prepared by known methods, is reacted with a suitably substituted compound of formula (X), wherein $PG^3$ is a suitably selected nitrogen protecting group such as —C(O)CH$_3$, —C(O)OCH$_2$CH$_3$, —C(O)O-t-butyl (Boc), —CHO, —C(O)OCH$_3$, —C(O)O—CH$_2$-phenyl, —C(O)-phenyl, —C(O)OCH$_2$CCl$_3$, —C(O)-(4-nitrophenyl), —C(O)CCl$_3$, —C(O)CF$_3$, —SO$_2$CH$_3$, —SO$_2$-phenyl, —SO$_2$-(4-nitrophenyl), or —SO$_2$CF$_3$, for example —C(O)CH$_3$, C(O)OCH$_2$CH$_3$ or —C(O)O-t-butyl (Boc), a known compound or compound prepared by known methods; wherein the compound of formula (IX-S) is present in an amount in the range of from about 1.0 to about 4.0 molar equivalents, for example about 1.5 molar equivalents; in a first organic solvent such as ethanol, isopropanol, acetonitrile or 2-methyl-THF, for example in 2-methyl-THF; at a temperature in the range of from about room temperature to about 80° C., for example at about 80° C.; to yield the corresponding compound of formula (XI-S).

The compound of formula (XI-S) is reacted with a compound of formula (VI-B), a known compound or compound prepared by known methods; wherein the compound of formula (VI-B) is present in an amount in the range of from about 1.0 to about 3.0 molar equivalents, for example about 1.5 molar equivalents; in the presence of a suitably selected coupling agent system such as DIAD and PPh$_3$, DEAD and PPh$_3$, or ADDP and PBu$_3$, for example DIAD and PPh$_3$; wherein the PPh$_3$ of the coupling agent system is optionally present on a solid support; and wherein the coupling agent system is present in, for example, an amount in the range of from about 1.0 to about 2.0 molar equivalents, for example 1.2 molar equivalents; in a second organic solvent such as THF, 2-methyl-THF, toluene, acetonitrile, ethyl acetate or DMF, for example in 2-methyl-THF; at a temperature in the range of from about −10° C. to about room temperature, for example at about 5° C.; to yield the corresponding compound of formula (XII-S).

The compound of formula (XII-S) is de-protected according to known methods, to yield the corresponding compound of formula (I-S). For example, wherein $PG^3$ is —C(O)O—C(CH$_3$)$_3$ (BOC), the compound of formula (XII-S) may be de-protected by reacting with a suitably selected acid such as HCl, and the like; alternatively, wherein $PG^3$ is —C(O)—CH$_3$ or —C(O)O—CH$_2$CH$_3$, the compound of formula (XII-S) may be de-protected by reacting with a suitably selected base such as NaOH, and the like. One skilled in the art will further recognize that the compound of formula (XII-S) may be de-protected as a discrete or separate reaction step (as described for example in Example 7, Step B, which follows herein); or alternatively, in the work-up of the compound of formula (XII-S) (as described for example, in Examples 10 and 12, which follow herein).

The compound of formula (X) may be prepared by protecting guanidine according to known methods. For example, the compound of formula (X), wherein $PG^3$ is Boc may be prepared by reacting guanidine with BOC$_2$O, according to known methods. The preparation of a compound of formula (X) wherein $PG^3$ is Boc is outlined in more detail in Example 8 which follows herein.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum or a syrup.

Example 1

(E)-2-[(dimethylamino)-methylene]-3-oxobutanenitrile

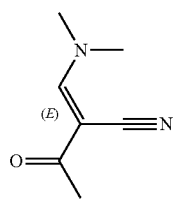

A 2000 ml 3-neck Morton flask was equipped with an overhead stirrer, a $N_2$ inlet, and a thermocouple. The flask was charged with water (500 g) and 36% hydrochloric acid (192.00 g, 12.18 mol). The resultant clear solution was stirred and cooled to room temperature, whereupon 3-aminocrotononitrile (100.19 g, 1.17 mol) was added portion-wise over about 15 minutes. The resultant solution was stirred at room temperature for about 1 h. The aqueous reaction mixture was then extracted twice with ethyl acetate (450.2 g portions).

The organic extracts were then charged to a clean 2000 ml 3-neck Morton flask equipped with an overhead stirrer, an addition funnel, and a thermocouple. Stirring was initiated and dimethylformamide dimethyl acetal (165.11 g, 1.39 mol) was added dropwise via the addition funnel over about 18 minutes, while maintaining the internal temperature at <34° C. The resultant solution was stirred at room temperature for about 2 h.

A solution of sodium bicarbonate (20.14 g, 0.24 mol) in water (200.0 g) was then added and the resultant biphasic mixture was stirred vigorously at room temperature for about 20 minutes. The layers were separated and the organic layer was dried over $MgSO_4$, filtered and concentrated by rotary evaporation to yield an oil, which rapidly crystallized to yield the title compound as a low melting solid.

$^1$H NMR (300 MHz, CDCl$_3$): δ 7.82 (s, 1H), 3.41 (s, 3H), 3.25 (s, 3H), 2.35 (s, 3H)

MS: (CI): m/z 139 (M$^+$+1), 161 (M$^+$+Na)

Elemental Analysis for $C_7H_{10}N_2O\times0.17\ H_2O$: Calculated: C, 59.53; H, 7.38; N, 19.84, $H_2O$, 2.17. Found: C, 59.12; H, 7.62; N, 19.85, $H_2O$, 2.04.

Example 2

1-Methyl-4-Piperidinepropanol

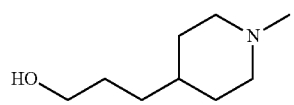

A solution of 4-pyridinepropanol (100.0 g, 0.70 mol) in water (200.0 g) was treated with glacial AcOH (83.84 g, 1.40 mol) and 10% Pd/C (50% wet; 16.00 g, 0.015 mol). The resultant slurry was then charged to a 500 ml Zipperclave pressure reactor. The unit was evacuated, stirring was initiated at 800 RPM and the unit was charged with 300 psi of hydrogen. The reaction mixture was heated at between 35-39° C. for about 10 h.

The resultant mixture was cooled to room temperature and formaldehyde (59.36 g, 0.73 mol) was added in a single portion. The Zipperclave unit was sealed, evacuated, and the resultant mixture was stirred at 800 RPM and heated to 39° C. The unit was then pressurized with 300 psi of hydrogen and the temperature was raised to 45° C., which was maintained throughout the reaction. Hydrogen uptake ceased in about 1 h, although the reaction mixture was maintained under hydrogen pressure for an additional 0.5 h.

The resultant mixture was then cooled to room temperature and filtered over a Celite® pad, which was washed with water (30 g). The combined filtrate and washes were cooled in an ice bath and stirred during the addition of 50% NaOH (81.00 g, 1.01 mol). The addition required 15 minutes and the temperature was maintained at <40° C. The product separated as an oil and the mixture was extracted twice with 2-Me-THF (86.00 g portions). The organic extracts were filtered through Celite® and concentrated by rotary evaporation at 65° C. to yield an oil. A small amount of residual sodium acetate was removed by filtration through a coarse porosity sintered glass funnel to yield the title compound as an oil.

$^1$H NMR (300 MHz, CDCl$_3$): δ 3.61 (t, J=6.7 Hz, 2H), 2.83 (bd, J=11.6 Hz, 2H), 2.24 (s, 3H), 1.93-1.86 (bt, J=11.1 Hz, 3H), 1.71-1.67 (m, 2H), 1.60-1.55 (m, 2H), 1.33-1.22 (m, 5H)

MS: (CI): m/z 158 (M$^+$+1)

Example 3

1-Methyl-4-Piperidinepropanol

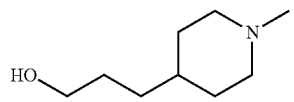

An Argonaut reaction vessel was charged with 4-pyridinepropanol (500.0 mg, 3.49 mmol) and 5% Rh/C (62% wet, 300.0 mg) in water (4.00 g). The resultant slurry was stirred at 500 RPM and the unit was pressurized with 300 psi of hydrogen. The resultant mixture was heated at 50° C. for about 4-4.5 h, during which time the hydrogen uptake ceased.

The resultant mixture was then cooled to room temperature and a 37% formaldehyde solution (340.0 mg, 4.19 mmol) was added in a single portion. The Argonaut vessel was sealed and the resultant slurry was stirred at 500 RPM, the unit was repressurized with 300 psi of hydrogen, and heated to 50° C. Hydrogen uptake ceased in about 1.2-1.5 h to yield the title compound, which was used in the next step without further purification or isolation.

HPLC-MS analysis of an aliquot showed only $C_9H_{19}NO$

MS: (CI): m/z 158 (M$^+$+1)

Example 4

1-Methyl-4-Piperidinepropanol

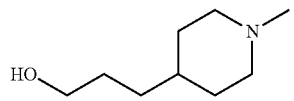

An Argonaut reaction vessel was charged with 4-pyridinepropanol (500.0 mg, 3.49 mmol), methanol (6 mL), acetic acid (2 mL), and 10% P/C (dry, 77 mg). The resultant slurry was stirred at 500 RPM and the unit was pressurized with 300 psi of hydrogen at 35° C. The resultant mixture was then stirred for 8 hours (until the hydrogen uptake was observed to cease).

The resultant mixture was then cooled to room temperature and a 37% formaldehyde solution (340.0 mg, 4.19 mmol) was added in a single portion. The Argonaut vessel was sealed and the resultant slurry was stirred at 500 RPM, the unit was re-pressurized with 300 psi of hydrogen, and heated to 35° C. Hydrogen uptake was observed to cease after about 20 min. The resultant mixture was filtered through a Celite® pad to remove the catalyst. The resultant solution was cooled to 0° C., and 50% NaOH solution was added to adjust the pH>12. The resultant mixture was then concentrated in vacuo, and the residue extracted with 2-Me-THF (3×10 mL). The combined organic phases was washed with brine (5 mL), dried (MgSO$_4$), and concentrated in vacuo to yield the title compound.

MS: (Cl): m/z 158 (M$^+$+1)

Example 5

N-Carbethoxyguanidine

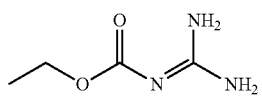

A 500 ml 4-neck Morton flask was equipped with an overhead stirrer, a N$_2$ inlet, and a thermocouple. The flask was charged with guanidine hydrochloride (22.19 g, 230.0 mmol) followed by absolute EtOH (59 g). The resultant mixture was stirred at ambient temperature for ~15-20 minutes to yield a solution, whereupon 21 wt % NaOEt/EtOH (74.82 g) was added in one portion, followed by an EtOH (4.0 g) rinse— NaCl precipitated immediately. The resultant cream suspension was stirred briefly at ambient temperature, then diethyl carbonate (27.71 g, 231.4 mmol) was added portion-wise in 3 approximately equal portions, followed by an EtOH (16.0 g) rinse. The cream suspension was stirred under N$_2$ at ambient temperature overnight.

The suspension was then cooled to ~2-3° C., stirred for 1 h, settled for 15-20 minutes and then filtered. The inorganic salts were washed with absolute EtOH (2×20 g portions) and then discarded. The combined EtOH filtrate and washes were evaporated to yield N-carbethoxyguanidine, which slowly solidified. The product was dried overnight in a vacuum oven at 56° C./50 Torr to remove as much EtOH as possible. The dried solid was a mixture of N-carbethoxyguanidine contaminated with some N,N'-bis-(carbethoxy)-guanidine. The crude product (~27.48 g) was recrystallized from 1,4-dioxane (290 g) after hot filtration to remove a small amount of residual NaCl. N-Carbethoxy guanidine crystallized from the hot filtrate almost immediately. The suspension was cooled to room temperature, filtered, and the solid was dried in a vacuum oven at 56° C./50 Torr overnight to yield the title compound as a crystalline solid.

mp: 97.0-99.0° C.

$^1$H NMR (300 MHz, DMSO-d$_6$): δ 6.80 (bs, 4H), 3.89 (q, J=7.0 Hz, 2H), 1.11 (t, J=7.0 Hz, 3H)

MS: (Cl): m/z 132 (M$^+$+1), 263 (2M$^+$+1)

Further concentration of the 1,4-dioxane mother liquors from above yielded a second crop of the title compound.

Example 6

2-(4-Methyl-5-cyano)-pyrimidinecarbamic acid ethyl ester

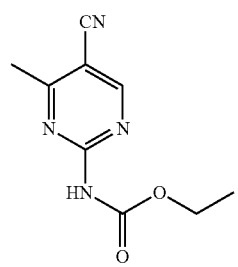

A 500 ml 4-neck Morton flask was equipped with an overhead stirrer, a N$_2$ inlet, a reflux condenser, and a thermocouple-temperature controller. The flask was charged with N-(carbethoxy)-guanidine (7.16 g, 50.04 mmol) followed by 2-methyltetrahydrofuran (2-MeTHF) (85.88 g) and (E)-2-[(dimethylamino)-methylene]-3-oxobutanenitrile (9.26 g, 65.0 mmol). The resultant suspension was stirred and heated to reflux (75° C.). The reaction was monitored by HPLC and was stopped after 50 h at 75° C.

The suspension was cooled to about 55° C. and filtered warm to remove un-reacted starting materials. The resultant solids were washed with 2-MeTHF (21.5 g) and the combined filtrate and washes were slowly cooled to room temperature. Crystals were observed upon cooling. The crystals were filtered, washed twice with MTBE (7.5 g) and then air dried overnight to yield the title compound as a crystalline solid.

mp: 167.0-168.0° C.

$^1$H NMR (300 MHz, DMSO-d$_6$): δ 10.96 (bs, 1H), 8.96 (s, 1H), 4.15 (q, J=7.1 Hz, 2H), 2.56 (s, 3H), 1.23 (t, J=7.1 Hz, 3H)

MS: (Cl): m/z 207 (M$^+$+1), 229 (M$^+$+Na), 435 (2M$^+$+Na)

Elemental Analysis for C$_6$H$_{10}$N$_4$O$_2$: Calculated: C, 52.42; H, 4.89; N, 27.17. Found: C, 52.10; H, 4.80; N, 27.26.

After cooling the combined MTBE/2-MeTHF filtrate and washes from above to −20° C., a second crop of the title compound was obtained.

Example 7

4-Methyl-2-[(3-(1-methyl-piperidin-4-yl)-propylamino]-pyrimidine-5-carbonitrile

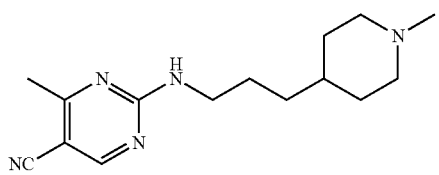

Step A: (5-Cyano-4-methyl-pyrimidin-2-yl)-[3-(1-methyl-piperidin-4-yl)-propyl]-carbamic acid ethyl ester A 50 ml Erlenmeyer flask was charged with 3-(1-methyl-piperidin-4-yl)-propan-1-ol (1.5 g, 9.42 mmol) followed by addition of 2-methyltetrahydrofuran (1.72 g). Anhydrous magnesium sulfate (0.7 g) was then added and the resultant suspension was stirred for 5 minutes. The solid was filtered off and washed with 2-methyltetrahydrofuran (2.0 g). The water content of the filtrate was determined to be KF=0.66%. The filtrate was transferred to a 100 ml 3-neck flask equipped with a stirrer, a thermocouple and an addition funnel followed by addition of triphenylphosphine (3.2 g, 12.1 mmol) and (5-cyano-4-methyl-pyrimidin-2-yl)-carbamic acid ethyl ester (2.0 g, 9.65 mmol). The resultant suspension was cooled to about 0-5° C. Diisopropyl azodicarboxylate (2.55 g, 11.98 mmol) was added via the addition funnel to the stirred suspension over about 1 h, while maintaining the temperature at about 0-5° C. After the addition, the resultant mixture was stirred at ambient temperature overnight. The reaction was monitored by HPLC.

The reaction mixture was quenched at about 20-30° C. with an HCl solution [prepared from 37% HCl (3.48 g, 34.8 mmol) and water (14.0 g, 777.8 mmol)]. The resultant biphasic mixture was cooled to ambient temperature and allowed to settle. The top organic layer was split off and the bottom aqueous layer was extracted with toluene (8.71 g). The aqueous layer was basified at ambient temperature by addition of a sodium hydroxide solution [prepared from NaOH (0.8 g, 20.0 mmol) and water (5.0 g)]. The desired product -(5-cyano-4-methyl-pyrimidin-2-yl)-[3-(1-methyl-piperidin-4-yl)-propyl]-carbamic acid ethyl ester—was extracted with 2-methyltetrahydrofuran (17.2 g). The organic layer was dried over anhydrous magnesium sulfate (4.0 g) and the solvent was removed by rotary evaporation to yield (5-cyano-4-methyl-pyrimidin-2-yl)-[3-(1-methyl-piperidin-4-yl)-propyl]-carbamic acid ethyl ester.

MS: (Cl): m/z 346 (M$^+$+1).

Step B: 4-Methyl-2-[3-(1-methyl-piperidin-4-yl)-propylamino]-pyrimidine-5-carbonitrile In a 100 ml 3-neck flask, (5-cyano-4-methyl-pyrimidin-2-yl)-[3-(1-methyl-piperidin-4-yl)-propyl]-carbamic acid ethyl ester (1.4 g, 4.05 mmol) was dissolved in MeOH (16.0 g). The resultant solution was cooled to about 0-5° C., and then a sodium hydroxide solution [prepared from NaOH (0.6 g) and water (1.2 g)] was added at about 0-5° C. The resultant mixture was stirred at 0° C., then warmed to ambient temperature over 3 h. The reaction was monitored by HPLC. The resultant mixture was concentrated by rotary evaporation at about 20-25° C. and the resultant solid was slurried in water (20 g), overnight at ambient temperature. The solid was collected by filtration, washed with water (20 g) and dried in a vacuum oven at about 70-80° C. overnight to yield the title compound.

$^1$H NMR (300 MHz, DMSO-d$_6$): δ 8.60 and 8.52 (singlets that coalesce upon heating to 80° C., 1H), 8.25-8.17 (m, 1H), 3.34-3.24 (m, 2H), 2.70 (bd, J=11.3 Hz, 2H), 2.41 and 2.38 (singlets that coalesce upon heating to 80° C., 3H), 2.10 (s, 3H), 1.77 (bt, J=10.9 Hz, 2H), 1.60-1.46 (m, 4H), 1.20-1.06 (m, 5H)

Elemental Analysis for C$_{16}$H$_{23}$N$_6$×0.08 H$_2$O: C, 65.56; H, 8.49; N, 25.48; H$_2$O, 0.52. Found: C, 65.30; H, 8.68; N, 25.04; H$_2$O, 0.33.

Example 8

N-(t-Butyloxycarbonyl)guanidine

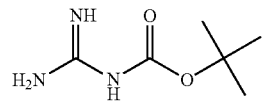

A 1000 ml 3-neck Morton flask was equipped with an overhead stirrer, a N$_2$ inlet, an addition funnel, and a thermocouple. The flask was charged with guanidine hydrochloride (22.76 g, 235.8 mmol) followed by 3.96M NaOH solution (prepared from 95.0 ml of 5M NaOH and 25 ml of water, 120 ml total). The resultant mixture was stirred to yield a solution and cooled to <2° C. A solution of (Boc)$_2$O (42.53 g, 189.0 mmol) in 1,4-dioxane (103.2 g) was added to the stirred mixture over 50 minutes while maintaining the temperature at <8° C. A solid precipitated from the resultant biphasic mixture during the (Boc)$_2$O/1,4-dioxane addition. The resultant white suspension was stirred at ice bath temperature for about 1.25 h.

After addition of water (200.00 g) the resultant mixture was evaporated to yield a solid comprising the crude product together with inorganic salts and a small amount of bis-Boc-guanidine. The solids were suspended in 2-Me-THF (344.00 g), the suspension was stirred and heated to reflux and maintained at reflux for about 1 h. The suspension was then cooled to about 55-60° C. and filtered warm to remove the inorganic salts. Evaporation of the 2-MeTHF yielded a solid. This solid was re-suspended in MTBE (37.00 g) and the resultant suspension was stirred at ambient temperature for ~1 h. The suspension was filtered, and the solid was washed with MTBE (18.5 g). The MTBE treatment was repeated again and the resultant product was air dried for several hours at ambient temperature. The product —N-(t-butyloxycarbonyl)-guanidine—was isolated as a solid.

$^1$H NMR (300 MHz, DMSO-d$_6$): δ6.74 (bs, 4H), 1.34 (s, 9H); MS: (Cl) m/z 160 (M$^+$+1), 319 (2M$^+$+1)

Example 9

(5-Cyano-4-methyl-pyrimidin-2-yl)-carbamic acid tert-butyl ester

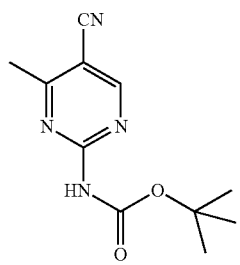 [SMILES: Cc1nc(NC(=O)OC(C)(C)C)ncc1C#N]

A 250 ml 3-neck flask was equipped with an overhead stirrer, thermocouple, reflux condenser and heating mantle. The flask was charged with (E)-2-acetyl-3-dimethylaminoacrylonitrile (8.93 g, 63.34 mmol), N-tert-butyloxycarbonyl-guanidine (10 g, 61.56 mmol) and 2-methyltetrahydrofuran (98.76 g). The resultant suspension was stirred and heated to reflux, whereupon the solids were observed to dissolve. The resultant mixture was stirred for about 6 hours, then concentrated by rotary evaporation to yield a solid which was triturated with water (120.00 g) to complete precipitation of the desired product. The resultant suspension was stirred for ~30 minutes at ambient temperature, then filtered and the wet solid washed twice with water (120.00 g) and dried in a vacuum oven at 75-80° C. under a $N_2$ bleed overnight to yield the title compound.

$^1$H NMR (300 MHz, $CH_3CN$-$d_3$): δ 8.71 (s, 1H), 8.49 (br s, 1H), 2.57 (s, 3H), 1.50 (s, 9H)

MS: (CI): m/z 257 ($M^+$+Na)

Elemental Analysis for $C_{11}H_{14}N_4O_2$: Calculated: C, 56.40; H, 6.02; N, 23.92. Found: C, 56.46; H, 5.96; N, 23.93.

Example 10

4-Methyl-2-[3-(1-methyl-piperidin-4-yl)-propylamino]-pyrimidine-5-carbonitrile

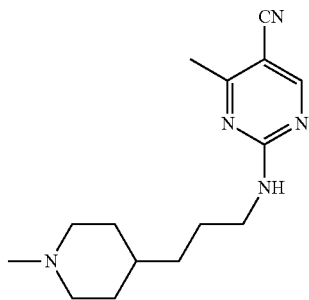 [SMILES: Cc1nc(NCCCC2CCN(C)CC2)ncc1C#N]

Step A: (5-Cyano-4-methyl-pyrimidin-2-yl)-[3-(1-methyl-piperidin-4-yl)-propyl]-carbamic acid tert-butyl ester A 200 ml Erlenmeyer flask was charged with 3-(1-methyl-piperidin-4-yl)-propan-1-ol (12.75 g, 80.11 mmol) followed by 2-methyltetrahydrofuran (146.0 g). Magnesium sulfate was added and the resultant suspension was stirred for 5 minutes. The solid was filtered off and washed with 2-methyltetrahydrofuran (14.6 g). The water content of the filtrate was determined to be KF=0.66%.

The filtrate was transferred to a 500 ml 3-neck flask equipped with an overhead stirrer, a thermocouple, and an addition funnel. Triphenylphosphine (30.2 g, 113.99 mmol) was added followed by addition of (5-cyano-4-methyl-pyrimidin-2-yl)-carbamic acid tert-butyl ester (17.0 g, 71.48 mmol). The resultant mixture was stirred until the solids were observed to dissolve. The resultant solution was cooled to about 0-5° C. and diisopropyl azodicarboxylate (DIAD) (23.91 g, 112.33 mmol) was added via the addition funnel to the stirred solution over ~50 minutes, while maintaining the temperature at about 0-5° C. After the addition, the resultant mixture was warmed to ambient temperature and stirred overnight. The reaction was monitored by HPLC. (5-Cyano-4-methyl-pyrimidin-2-yl)[3-(1-methyl-piperidin-4-yl)-propyl]-carbamic acid tert-butyl ester, in the resultant solution was used in the next step without further isolation and/or purification.

Step B: 4-Methyl-2-[3-(1-methyl-piperidin-4-yl)-propylamino]-pyrimidine-5-carbonitrile The suspension containing (5-cyano-4-methyl-pyrimidin-2-yl)[3-(1-methyl-piperidin-4-yl)-propyl]-carbamic acid tert-butyl ester, prepared as in STEP A above, was quenched at about 20-30° C. with HCl solution [prepared from 37% HCl (15.82 g, 158.34 mmol) and water (34.0 g, 1890 mmol)]. The resultant biphasic mixture was warmed to about 50-55° C. and stirred for about 1 hour. The de-protection was monitored by HPLC. Once the reaction was complete, water (70 g) was added and the resultant biphasic mixture was cooled to ambient temperature and allowed to settle. The top organic layer was split off, and the bottom aqueous layer was extracted with toluene (69.7 g).

The desired product (the title compound) was contained in the aqueous layer which was treated as follows. A 500 ml 3-neck flask was equipped with an overhead stirrer, a thermocouple, and an addition funnel. Water (170.0 g) and sodium hydroxide (7.0 g) were added. A solution was achieved with stirring. MeOH (26.92 g) was added and the resultant solution was cooled to about 20-25° C. The product containing aqueous solution was added via the addition funnel over ~40 minutes. A solid precipitated out during the addition. After the addition was complete, the suspension was stirred for ~30 minutes and then filtered. The resultant wet solid was washed with water (170.0 g) and then dried in a vacuum oven at 70° C. overnight to yield the title compound.

$^1$H NMR (300 MHz, DMSO-$d_6$): δ 8.60 and 8.52 (singlets that coalesce upon heating to 80° C., 1H), 8.25-8.17 (m, 1H), 3.32-3.24 (m, 2H), 2.70 (bd, J=10.9 Hz, 2H), 2.41 and 2.38 (singlets that coalesce upon heating to 80° C., 3H), 2.11 (s, 3H), 1.77 (bt, J=10.8 Hz, 2H), 1.58-1.46 (m, 4H), 1.20-1.06 (m, 5H)

MS: (CI): m/z 274 ($M^+$+1)

Elemental Analysis for $C_{16}H_{23}N_6$: Calculated: C, 65.90; H, 8.48; N, 25.62. Found: C, 66.00; H, 8.57; N, 25.38.

Example 11

N-(4-Methyl-5-cyano-2-pyrimidinyl)-acetamide

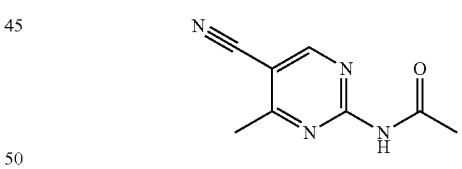

A 250 ml 3-neck flask was equipped with an overhead stirrer, reflux condenser, and a thermocouple. The flask was charged with 2-amino-4-methyl-5-cyanopyrimidine (8.00 g, 59.64 mmol) and an anhydrous NaOAc ((0.035 g, 0.43 mmol) in a mixture of HOAc (16.00 g, 266.43 mmol) and $Ac_2O$ (16.00 g, 156.72 mmol). The resultant suspension was stirred and heated to 115° C. to yield a brown suspension, which was stirred at 115° C. for 2 h during which time all starting material dissolved to yield a solution. The resultant mixture was heated at 115° C. for 6.5 hours and then cooled to room temperature to afford a suspension. Toluene (69.70 g) was added to the suspension, and the resultant mixture was then heated to about 108-114° C. to distill about 70 ml of solvent atmospherically (solution was effected at 70° C.). The resultant solution was cooled, fresh toluene (69.70 g) was added, and about 90 ml of solvent was distilled atmospherically at about 110-115° C. The resultant solution was cooled to 90° C., whereupon the mixture began to solidify. Toluene (8.7 g) and heptane (61.2 g) were added and the resultant suspension was stirred and gradually cooled to room temperature. After stirring at room temperature for 1 h, the suspension was filtered and the solid was washed twice with heptane (27.2 g portions) and then dried in a vacuum oven at 70° C. overnight. The title compound —N-(4-Methyl-5-cyano-2-pyrimidinyl)-acetamide—was isolated as a solid.

mp: 195.0-196.0° C.

$^1$H NMR (300 MHz, DMSO-d$_6$): δ 11.03 (bs, 1H), 8.99 (s, 1H), 2.58 (s, 3H), 2.23 (s, 3H); MS: (Cl)
m/z 177 (M$^+$+1), 375 (2M$^+$+Na)

Example 12

4-Methyl-2-[3-(1-methyl-piperidin-4-yl)-propylamino]-pyrimidine-5-carbonitrile

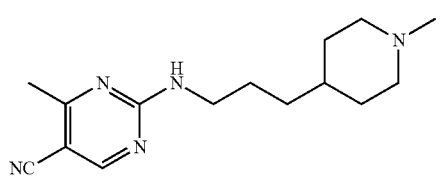

A 100 ml 3-neck flask equipped with a magnetic stir-bar, a thermocouple and an addition funnel was charged with N-(5-cyano-4-methyl-pyrimidin-2-yl)-acetamide (1.00 g, 5.39 mmol) followed by EtOAc (9.02 g). The resultant mixture was stirred to yield a solution and then 3-(1-methyl-piperidin-4-yl)-propan-1-ol (1.70 g, 10.81 mmol) was added, followed by addition of Ph$_3$P (2.85 g, 10.76 mmol). The resultant solution was cooled to 0-5° C. and diisopropyl azodicarboxylate (DIAD) (2.30 g, 10.81 mmol) was added using the addition funnel, while maintaining the reaction temperature below 10° C. After the addition was complete, the resultant mixture was warmed to ambient temperature and stirred at 20-25° C. overnight.

The resultant mixture was treated at 20-25° C. with a dilute HCl solution (37% HCl (4.80 g) diluted with water (15.00 g)), followed by EtOAc (9.02 g) and water (10.00 g). The resultant mixture was settled and the top organic layer was removed. The acidic aqueous layer was stirred at room temperature for 1 h to yield a mixture (which contained the hydrolysis product, N-(5-cyano-4-methyl-pyrimidin-2-yl)-N-[3-(1-methyl-piperidin-4-yl)-propyl]-acetamide). The aqueous layer was extracted one time with EtOAc (9.02 g). 2-Methyl-THF (8.60 g) was added and the pH of the biphasic mixture was adjusted to about pH=12 by addition of 6N NaOH (9.69 g). The aqueous layer was removed and the 2-Me-THF layer was diluted with 2-MeT-HF (8.60 g) and dried with MgSO$_4$ (1.0 g). The pH of the dried 2-MeTHF solution was adjusted to about pH=1 by dropwise addition of 5-6N HCl/IPA, whereupon the HCl salt of the title compound precipitated. The solid was filtered, dissolved in EtOH (3.95 g) and the pH was adjusted to about pH=12 using 6N NaOH (4.85 g). The solid which precipitated during the addition was filtered, washed with water (10.00 g) and dried in a vacuum oven at 60-70° C. for 5 h to yield the title compound as a solid.

$^1$H NMR (300 MHz, DMSO-d$_6$): δ 8.60 and 8.52 (singlets, 1H), 8.25-8.19 (m, 1H), 3.33-3.24 (m, 2H), 2.70 (bd, J=10.3 Hz, 2H), 2.41 and 2.38 (singlets that coalesce upon heating to 80° C., 3H), 2.11 (s, 3H), 1.77 (bt, J=10.7 Hz, 2H), 1.55-1.46 (m, 4H), 1.20-1.03 (m, 5H)

MS: (Cl): m/z 274 (M$^+$+1)

Example 13

N,N'-Di(benzyloxycarbonyl)guanidine

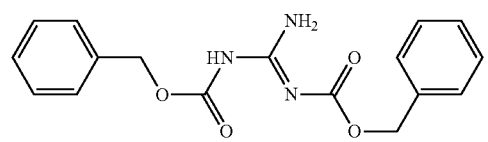 [SMILES: N/C(=N\C(=O)OCc1ccccc1)NC(=O)OCc1ccccc1]

A 100 L glass lined reactor equipped with a mechanical agitator, cooling jacket, condenser, and addition lines was charged with THF (15.53 kg) and guanidine HCl (3.10 kg, 32.02 mol). To the resultant slurry was added purified water (5.00 kg) and 50% sodium hydroxide solution (8.61 kg, 100.75 mol). The resultant slurry was cooled to 4-6° C. and benzyl chloroformate (13.02 kg, 72.51 mol) was slowly added over a 3.5-hour period, while keeping the temperature below 10° C. The resultant slurry was stirred for 2 hours at a temperature between 5-10° C. The slurry was then filtered and the solids washed with THF (5.58 kg).

The wet solids were then charged to the 100 L reactor and purified water (35.0 kg) was added. The resultant slurry was stirred for 30 minutes and filtered to remove any remaining inorganic salts. The solids were washed again with purified water (10.0 kg). The wet solids were charged again to the 100 L reactor and methanol (23.0 kg) was added. The resultant slurry was stirred for 30 minutes and filtered. The solids were washed with methanol (7.0 kg) and dried under 29 mm of vacuum at 60-65° C. to yield the title compound.

MS: (Cl): m/z 328 (M$^+$+1)

1H NMR (300 MHz, DMSO-d$_6$): δ10.89 (s, 1H), 8.69 (s, 2H), 7.36 (s, 10H), 5.11 (s, 4H)

Elemental Analysis for C$_{17}$H$_{17}$N$_3$O$_4$: Calculated: C, 62.38; H, 5.23; N, 12.84. Found: C, 62.41; H, 5.29; N, 12.86.

Example 14

N-[3-(1-methylpiperidin-4-yl)-propyl]-N,N'-di-cbz-guanidine

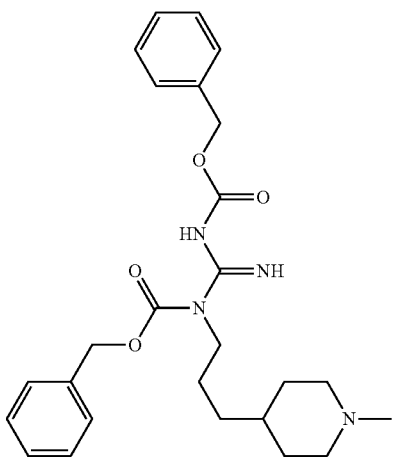 [SMILES: CN1CCC(CCCN(C(=N)NC(=O)OCc2ccccc2)C(=O)OCc2ccccc2)CC1]

To a 20 L carboy was charged 2-methyl-THF (8.00 kg) and 3-(1-methylpiperidin-4-yl)propan-1-ol (2.80 kg 17.62 mol). To the resultant solution were added molecular sieves (0.28 kg) and the resultant slurry was stirred until the water content was below 0.1% as tested by KF. The resultant solution was then filtered over Celite® and then charged to a 100 L glass-lined reactor, with 2-methyl-THF (17.52 kg) added. Triphenylphosphine (5.38 kg, 20.29 kg), and N,N'-di-Cbz-guanidine (5.77 kg 17.62 mol) were charged under a nitrogen blanket to the stirring solution. The reactor walls were rinsed with 2-methyl-THF (2.00 kg). The resultant suspension was cooled to between about −10 and about 0° C. and a solution of diisopropyl azodicarboxylate (4.41 kg 20.26 mol) and 2-methyl-THF (8.00 kg) was added while keeping the reaction temperature below 5° C. The resultant solution was then slowly warmed to about 15-20° C. over a 30-minute period.

After reaction completion a pre-made solution of 36.5% hydrochloric acid (2.61 kg 26.12 mol) and purified water (25.70 kg) was added at a temperature of about 15-20° C. Toluene (15.80 kg) was added, the resultant mixture was then stirred for 15 minutes and settled for 20 minutes. The water layer was retained and the 2-methyl-THF/toluene layer was discarded. The resultant mixture was extracted sequentially three times with toluene (35.0 kg), discarding the toluene layer after each extraction.

To the extracted water/product layer in the 100 L reactor was added ethanol (200 proof, 4.42 kg) and purified water (48.00 kg). To the resultant, stirring solution was added 6N sodium hydroxide (5.54 kg 29.10 mol) slowly while keeping the temperature between about 15-20° C. The resultant suspension was stirred for 1 hour, filtered and washed with purified water (29.00 kg). The wet solids were dried in a vacuum oven at about 40-45° C. to yield the title compound.

Example 15

N-[3-(N-methyl-4-piperidinyl)-1-propyl]guanidine

A 13 gal (50 liter) Hastelloy pressure reactor equipped with a mechanical agitator, cooling/heating jacket, and addition lines was charged with a solution of 95/5 EtOH/IPA (27.00 kg) and N-[3-(1-methylpiperidin-4-yl)-propyl]-N,N'-di-Cbz-guanidine (7.28 kg, 14.97 mol). To the resultant solution, under nitrogen, was then added 10% Pd/C (50% wet, 0.50 kg). The reactor was sealed and sequentially placed under vacuum, nitrogen and vacuum to displace any air in the system. The reaction was stirred at 1000 RPM and 300-350 PSI of hydrogen while keeping the temperature below 35° C. using cooling water on the jacket. The reaction ceased to be exothermic after approximately 1.5 hours and was stirred for an additional hour at 300-350 PSI. The resultant slurry was filtered over Celite® to yield a solution containing the title compound. The solution was stored at 5° C. and used in the next step without further isolation or purification.

Example 16

4-Methyl-2-[3-(1-methyl-piperidin-4-yl)-propylamino]-pyrimidine-5-carbonitrile

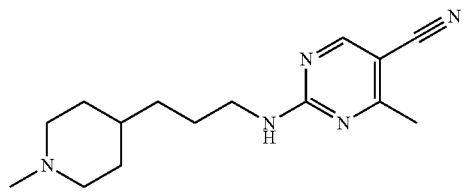 [SMILES: Cc1nc(NCCCC2CCN(C)CC2)ncc1C#N]

In a 100 L glass-lined reactor, a solution of (E)-2-[(dimethylamino)methylene]-3-oxobutanenitrile in ethanol/2-propanol (4.48 kg, 32.43 mol in 8.81 kg of ethanol/2-propanol) was added at 20-25° C. to a stirring solution of N-[3-(N-methyl-4-piperidinyl)-1-propyl]guanidine in ethanol/2-propanol (5.41 kg, 27.28 mol in 28.35 kg of ethanol/2-propanol). The resultant mixture was heated for 1.5 h at reflux, followed by an additional charge of (E)-2-[(dimethylamino)methylene]-3-oxobutanenitrile in ethanol/2-propanol (2.02 kg, 14.57 mol in 3.96 kg of ethanol/2-propanol). The resultant mixture was stirred and cooled to 70-75° C. and then potassium carbonate (7.50 kg, 54.26 mol) was added. The resultant mixture was heated to reflux until the reaction was deemed complete by HPLC. When the reaction was deemed complete, about 35-40 L of solvent was removed via atmospheric distillation. The heating was discontinued and purified water (80.00 kg) was added to the resultant suspension, which was then cooled to 20-25° C. and stirred for about 1 h. The resultant suspension was then further cooled to 0-5° C. and aged for 30 min. The solid was filtered, washed with purified water (40.00 kg) and dried at 75-80° C. under vacuum to yield the title compound.

In a 100 L glass-lined reactor, the solid title compound (6.08 kg, 21.4 mol) was dissolved in 2-propanol (30.00 kg) at 70-75° C. The resultant solution was cooled to 48-52° C. over 30 minutes and then heptane (43.00 kg) was added to the heavy slurry. The suspension was stirred at 30-35° C. for 10-15 min and then cooled to 0-5° C. and aged for 30 minutes. The solid was filtered, washed with heptane (12.00 kg) and dried at 75-80° C. under vacuum to yield the title compound.

$^1$H NMR (300 MHz, DMSO-d$_6$): δ 8.60 and 8.52 (singlets that coalesce upon heating to 80° C., 1H), 8.25-8.17 (m, 1H), 3.33-3.24 (m, 2H), 2.70 (bd, J=10.0 Hz, 2H), 2.41 and 2.38 (singlets that coalesce upon heating to 80° C., 3H), 2.11 (s, 3H), 1.77 (bt, J=10.7 Hz, 2H), 1.55-1.45 (m, 4H), 1.20-1.06 (m, 5H)

MS: (CI): m/z 274 (M$^+$+1)

Elemental Analysis for $C_{16}H_{23}N_6$: Calculated: C, 65.90; H, 8.48; N, 25.62. Found: C, 66.00; H, 8.80; N, 25.50.

In the experimental procedures as described in Example 17 through Example 31 reactions were typically monitored by a combination of mass spec and HPLC. HPLC conditions were as follows:

Column: Agilent ZORBAX® Eclipse XDB-C8, 5 μm, 4.6×150 mm

Flow rate: 1 mL/min

Mobile phases: acetonitrile with 0.05% TFA and water with 0.05% TFA

Gradient: 1% acetonitrile/99% water to 99% acetonitrile/1% water ramp over 8 min, then hold at 99% acetonitrile/1% water for 2 minutes.

Example 17

N,N'-Di(benzyloxycarbonyl)guanidine

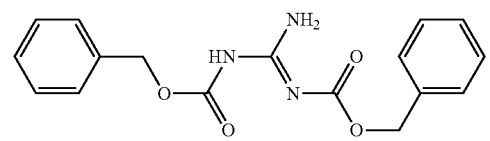 [SMILES: N/C(=N\C(=O)OCc1ccccc1)NC(=O)OCc1ccccc1]

To a 5-L jacketed reactor equipped with an overhead mechanical stirrer, thermocouple probe and dynamic nitrogen line were added the guanidine hydrochloride (119.7 g, 1.25 moles), NaOH (250 g, 6.26 moles) and deionized water (1.3 L). The resultant mixture was agitated until a homogeneous mixture was obtained. Methylene chloride (2.5 L) was then added and the biphasic mixture was cooled to 0° C. using an external chiller. To the resultant mixture was then added benzyl chloroformate (641.6 g, 3.76 moles) (utilizing a J-Kem dose controller) over a 3-hour period. Cooling was adjusted to maintain an internal temperature of 0° C. during the addition. The resultant heterogeneous mixture was aged, with agitation, at 0° C. for 20 hours. The resultant mixture was then warmed to room temperature and filtered, reserving the filter cake. The layers of filtrate were separated, and the aqueous layer was extracted with methylene chloride (2×1.0 L). The organic layers were combined, washed with water (2.0 L), dried over $MgSO_4$, and filtered. The solvent was removed under vacuum to yield a slurry. The solids were collected by filtration. The filtrate was again concentrated and a second crop of solids was collected. The two crops plus the filter cake from the initial filtration of the reaction were combined and dried in a vacuum oven (50° C.) for 18 hours to yield a residue.

The residue was added to a 5-liter jacked reactor equipped with an overhead mechanical stirrer, thermocouple probe, reflux condenser and dynamic nitrogen line. Methanol (2.0 L) was added and the resultant heterogeneous mixture was heated to reflux (~65° C.) for one hour, then cooled to room temperature and the solids were collected by filtration. The filter cake was dried in a vacuum oven (60° C.) for 24 hours to yield the title compound as a crystalline solid.

$^1$H-NMR: (400 MHz, DMSO-$d_6$) δ, 10.88 (br s, 1H), 8.67 (br s, 2H), 7.40-7.25 (m, 10H), 5.10 (s, 4H)

MS (electrospray): exact mass calculated for $C_{17}H_{17}N_3O_4$, 327.12; m/z found, 328.1 [M+H]+

Example 18

3-(1-methyl-piperidin-4-yl)-propan-1-ol

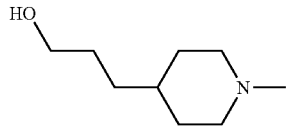

To a 2.25-L Parr reaction flask equipped with a heating mantle, and internal temperature probe were added 4-pyridinepropanol (72.87 g, 530 mmol), acetic acid (450 mL), and 10% Pd/C (10.73 g). The bottle was affixed to a Parr shaker and subjected to an atmosphere of $H_{2(g)}$ at 60 psi and 50° C. for ~7 hours. After hydrogen uptake slowed drastically, the resultant mixture was left under an atmosphere of 60 psi $H_{2(g)}$ with shaking for an additional 17 h. The bottle was cooled to room temperature and removed. A 37% formaldehyde solution was added (43.8 mL solution, 0.583 mmol) and the resultant mixture was returned to the Parr shaker and subjected to an atmosphere of $H_{2(g)}$ at 60 psi, room temperature for ~1 hour. The resultant mixture was filtered to remove palladium and then concentrated. The concentrate was taken up in water (300 mL) and the pH was adjusted to pH>12 with 50% NaOH solution. The aqueous layer was then extracted with ethyl acetate (3×350 mL). The combined organic layers were washed with brine, dried with magnesium sulfate, filtered, and concentrated to yield an oil.

The oil was taken up in methanol (450 mL) and then $K_2CO_3$ was added (30 g, 217 mmol). The resultant mixture was stirred for 3 h under $N_{2(g)}$. The resultant mixture was then filtered, concentrated and partitioned between water (350 mL) and ethyl acetate (350 mL). The aqueous layer was extracted twice more with ethyl acetate and the organic layers were combined, washed with brine, dried with magnesium sulfate, filtered, and concentrated to yield the title compound as an oil.

$^1$H-NMR: (400 MHz, CDCl$_3$) δ, 3.63 (t, J=6.6 Hz, 2H), 2.85-2.82 (m, 2H), 2.25 (s, 3H), 1.89 (t, J=11.2 Hz, 2H), 1.69-1.67 (m, 2H), 1.61-1.54 (m, 2H), 1.32-1.22 (m, 5H)

MS (electrospray): exact mass calculated for $C_9H_{19}NO$, 157.15; m/z found, 158.1 [M+H]+

Example 19

N-[3-(1-methyl-piperidin-4-yl)-propyl]-N,N'-di-cbz-guanidine

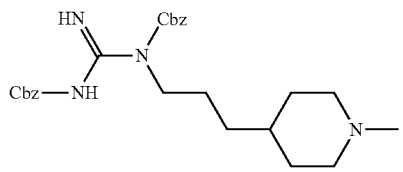 [SMILES: CN1CCC(CCCN(C(=N)NC(=O)OCc2ccccc2)C(=O)OCc2ccccc2)CC1]

To a 20-L jacketed reactor equipped with an overhead mechanical stirrer, thermocouple probe and dynamic nitrogen line was added anhydrous THF (14.25 liters). The stirring was set at 80 rpm and Polymer Labs (Varian) PL-TPP resin (1.0 Kg, 1.48 moles) was added (one portion) followed by addition of N,N'-di-cbz-guanidine (323.3 g, 0.987 moles) (one portion). 3-(1-Methyl-piperidin-4-yl)-propan-1-ol (155.3 g, 0.987 moles) dissolved in THF (500 mL) was then added to the resultant mixture via cannula transfer. The cannula, reactor sides and impeller shaft were all washed with THF (2.0 liters) and the wash solvent added to the reactor. The stirring was increased to 140 rpm and the resultant mixture cooled to an internal temperature of 10° C. DIAD (299.4 g, 1.48 moles) was added via a slow addition (utilizing a J-Kem dose controller) over 1.5 hours, with the cooling was adjusted to maintain an internal temperature below 12° C. Once the addition was complete, the resultant mixture was slowly warmed to 28° C. over a 1.5-hour period. The reactor was drained and rinsed with toluene. The wash toluene was added to the reaction mixture. The resin was removed by filtration and the filter cake was washed with toluene (2× the volume of the filter cake). The solvents were removed under reduced pressure to yield a residue.

The residue was partitioned between 0.5 M HCl (2.0 L) and ethyl acetate (2.0 L). The layers were separated and the aqueous layer was adjusted to pH ~10 with the slow addition of solid Na$_2$CO$_3$. The basic aqueous layer was extracted with ethyl acetate (2×1.0 L). The organic layers were combined, dried over MgSO$_4$, filtered and concentrated under reduced pressure to yield a slurry (~0.5 L of ethyl acetate remaining). Heptane (1.5 L) was added to the slurry and the resultant mixture was allowed to stir at room temperature for 1 hour. The solids were then collected by filtration. The filter cake was dried in a vacuum oven (50° C.) for 12 hours to yield the title compound as a solid.

The organic layers from the above workup were found to contain a large amount of the desired product. Both of the reserved organic layers were combined and concentrated to yield a residue. The residue was partitioned between 1.0 M HCl (500 mL) and toluene (500 mL) and a heterogeneous

Example 20

N-[3-(1-methyl-piperidin-4-yl)-propyl]-guanidine

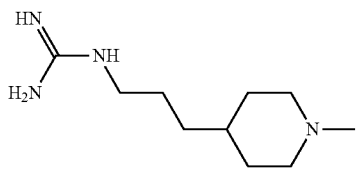

To a 1-L round bottom flask were added N-[3-(1-methyl-piperidin-4-yl)-propyl]-N,N'-di-cbz-guanidine (140.6 g, 0.301 moles) and ethanol (500 mL, 200 proof). The flask was equipped with a heating mantle and warmed to 50° C. Once a yellow homogeneous solution was obtained, the heating mantle was exchanged for an ice bath and the mixture cooled to an internal temperature of 10° C. The resultant cold mixture was transferred to a 2.25 liter Parr bottle equipped with a thermocouple probe, and 10% Pd on Carbon (10 wt. %) in one portion. The bottle was charged with $H_{2(g)}$ (60 psi). The Parr bottle was kept pressurized with hydrogen gas for 15 minutes, then evacuated, re-pressurized with $H_{2(g)}$ (60 psi) and allowed to shake for an additional hour. The catalyst was removed by filtration (Zap-Cap) and washed with ethanol (300 ml, 200 proof). The solvent was removed under pressure to yield the title compound.

$^1$H-NMR: (400 MHz, MeOD) δ, 3.14 (t, J=7.1 Hz, 2H), 2.89-2.82 (m, 2H), 2.25 (s, 3H), 2.03-1.93 (m, 2H), 1.77-1.67 (m, 2H), 1.64-1.55 (m, 2H), 1.34-1.20 (m, 5H)

MS (electrospray): exact mass calculated for $C_{10}H_{22}N_4$, 198.18; m/z found, 199.1 [M+H]+

Example 21

3-Oxo-butyronitrile

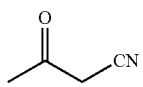

(E+Z)-3-amino-2-butenenitrile (115 g, 1.41 mol) was stirred in 2.0 M HCl (1.15 L) at room temperature for two hours. The resultant mixture was extracted with ethyl acetate (2×1.15 L), the organic layers were combined, and the solvent removed under vacuum yielding the title compound as an oil.

$^1$H-NMR: (400 MHz, CDCl$_3$) δ, 3.47 (s, 2H), 2.36 (s, 3H)

Example 22

(E)-2-[(dimethylamino)-methylene]-3-oxobutanenitrile

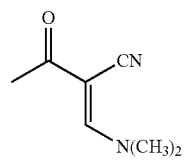

3-Oxo-butyronitrile (113 g, 1.36 mol) and DMF.DMA (215 g, 1.81 mol) were heated to 80° C. for two hours. The solvents were then removed under vacuum to yield a solid. The solid was partitioned between ethyl acetate (1.5 L) and saturated sodium bicarbonate solution (1 L). The layers were separated and the aqueous layer was extracted with ethyl acetate (1.5 L). The organic layers were combined and the solvent removed under vacuum to yield the title compound as a solid.

$^1$H-NMR: (400 MHz, CDCl$_3$) δ, 7.80 (s, 1H), 3.40 (s, 3H), 3.24 (2, 3H), 2.34 (s, 3H)

Example 23

2-acetyl-3-ethoxy-acrylonitrile

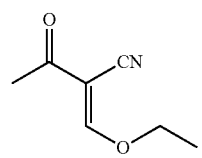

3-Oxo-butyronitrile (4.94 g, 60.9 mmol), triethylorthoformate (15.0 mL, 90.2 mmol), and acetic anhydride (0.3 mL, 2.7 mmol) were warmed to about 95-115° C. for about 1 hours, over which time a distillate was collected and discarded. After cooling the resultant mixture to room temperature, hexanes were added and a precipitate formed. The resultant mixture was filtered and the solids washed with hexanes, to yield the title compound as a solid.

$^1$H-NMR: (400 MHz, CDCl$_3$) δ, 8.01 (s, 1H), 4.37 (q, J=7.3 Hz, 2H), 2.39 (s, 3H), 1.46 (t, J=7.1 Hz, 3H).

Example 24

4-Methyl-2-[3-(1-methyl-piperidin-4-yl)-propylamino]-pyrimidine-5-carbonitrile

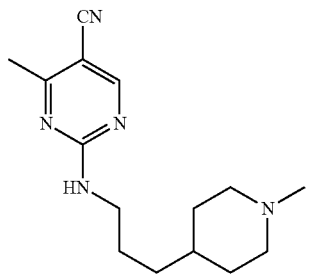

To a 5-L round-bottom flask equipped with overhead mechanical stirrer, nitrogen inlet, and thermocouple probe were added 2-acetyl-3-dimethylamino-acrylonitrile (103.65 g, 0.75 mol), anhydrous potassium carbonate (powdered, not granular) (165.85 g, 1.2 mol), and N-[3-(1-methyl-piperidin-4-yl)-propyl]-guanidine (119.02 g, 0.60 mol) in ethanol (2.125 L). The resultant mixture was heated to reflux with stirring and held for 24 h. The resultant mixture was then concentration and the resultant residue partitioned between ethyl acetate (1.5 L) and 1 N NaOH (1.5 L). The layers were separated and the aqueous layer was extracted with additional ethyl acetate (2×1.5 L). The combined organic layers were concentrated to yield the title compound as a solid.

$^1$H-NMR: (400 MHz, MeOD) δ, 8.46 and 8.37 (two singlets that coalesce if spectrum is observed in DMSO at 100° C., 1H), 3.43-3.36 (m, 2H), 2.88-2.81 (m, 2H), 2.48, 2.43 (two singlets that coalesce if spectrum is observed in DMSO at 100° C., 3H), 2.24 (2, 3H), 2.03-1.93 (m, 2H), 1.76-1.67 (m, 2H), 1.66-1.56 (m, 2H), 1.36-1.16 (m, 5H)

MS (electrospray): exact mass calculated for $C_{15}H_{23}N_5$, 273.20; m/z found, 274.1 [M+H]+

Example 25

4-Methyl-2-[3-(1-methyl-piperidin-4-yl)-propylamino]-pyrimidine-5-carbonitrile

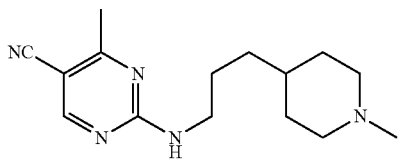 [SMILES: Cc1nc(NCCCC2CCN(C)CC2)ncc1C#N]

A flask containing sodium ethoxide (0.64 mL of a 21 wt % solution in ethanol, 1.7 mmol) and N-[3-(1-methyl-piperidin-4-yl)-propyl]-guanidine.HCl (200 mg, 0.85 mmol) in ethanol (2.45 mL) was aged for 15 minutes at room temperature. To the resultant mixture was then added 2-acetyl-3-ethoxy-acrylonitrile (148 mg, 1.06 mmol). The resultant mixture was warmed to 80° C. for 5 h, then cooled to room temperature and concentrated. The resultant residue was partitioned between 1 N NaOH and dichloromethane. After separation of the layers, the aqueous layer was extracted with additional dichloromethane (2×). The combined organic layers were dried over MgSO$_4$, filtered, and concentrated to yield the title compound as a solid.

Example 26

N,N',N"-tri-Boc-guanidine

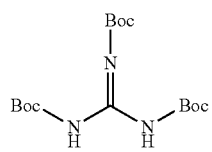

To a 300 mL, 3-neck, round bottom flask were added powdered KOH (2.94 g, 0.052 mol), Na$_2$CO$_3$ (5.54 g, 0.052 mol) and DMSO (50 mL). The resultant slurry was aged at room temperature for 5 min, then guanidine hydrochloride (5.0 g, 0.052 mol) was added. After an additional 5 min, di-t-butyldicarbonate (51.4 g, 0.23 mol) was added as a melt. The resultant mixture was warmed to 40° C. and aged for 65 h. The resultant mixture was cooled to 10° C. and poured into 0° C. water (1.0 L). The resultant precipitate was collected by filtration and purified by hot trituration in acetonitrile (500 mL) to yield N,N',N"-tri-Boc-guanidine.

$^1$H-NMR: (400 MHz, CDCl$_3$) δ, 1.51 (s, 27 Hz).

MS (electrospray): exact mass calculated for $C_{16}H_{29}N_3O_6$, 359.21; m/z found, 360.2 [M+H]+

Example 27

N-[3-(1-methylpiperidin-4-yl)-propyl]-N,N',N"-tri-Boc-guanidine

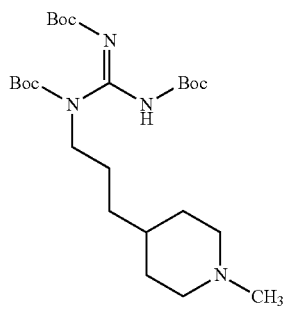

To a 100 mL, 3-neck, round bottom flask were added 3-(1-methyl-piperidin-4-yl)-propan-1-ol (1.91 g, 0.012 mol), Polymer Labs (Varian) PL-TPP resin (9.83 g, 0.014 mol), N,N',N"-tri-Boc-guanidine (4.36 g, 0.012 mol) and THF (anhydrous, 100 mL). The resultant mixture was stirred and cooled to 2° C., at which time DEAD (2.53 g, 0.014 mol) was added drop wise over 10 min. Upon completion of addition, the flask was warmed to room temperature, aged for 4 h and filtered to remove the resin bound oxide. The resultant cake was rinsed with THF (25 mL) and heptane (2×25 mL). The filtrates were combined, extracted with saturated aqueous NaHCO$_3$ (2×25 mL), dried over anhydrous MgSO$_4$, filtered and concentrated. The resultant residue was triturated in hot ethanol (25 mL), cooled to room temperature and filtered. The filtrate was concentrated to yield N-[3-(1-methylpiperidin-4-yl)-propyl]-N,N',N"-tri-Boc-guanidine.

$^1$H-NMR: (400 MHz, CDCl$_3$) δ, 10.64 (brs, 1H), 3.75 (t, J=7.1 Hz, 2H), 2.83-2.80 (m, 2H), 2.24 (s, 3H), 1.87 (t, J=10.1 Hz, 2H), 1.72-1.63 (m, 4H), 1.54-1.46 (m, 27H), 1.30-1.18 (m, 5H).

MS (electrospray): exact mass calculated for $C_{25}H_{46}N_4O_6$, 498.34; m/z found, 499.4 [M+H]+

Example 28

N-[3-(N-methyl-4-piperidinyl)-1-propyl]guanidine

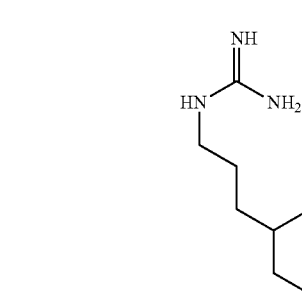

To a 200 mL round bottom flask were added N-[3-(1-methylpiperidin-4-yl)-propyl]-N,N',N''-tri-Boc-guanidine prepared as in Example 27 above (3.20 g, 0.0064 mol) and 1,4-dioxane (anhydrous, 50 mL). To the resultant stirred solution was added 4.0 M HCl in 1,4-dioxanes (6.42 mL, 0.026 mol) drop wise over 2.0 min. The resultant mixture was then warmed to 75° C., aged for 3 h then cooled to 0° C. A precipitate was formed. The bulk solvent was decanted and the solids were dried under vacuum for 12 h to yield N-[3-(N-methyl-4-piperidinyl)-1-propyl]guanidine, as its corresponding HCl salt.

$^1$H-NMR: (400 MHz, MeOD) δ, 3.14 (t, J=7.1 Hz, 2H), 2.89-2.82 (m, 2H), 2.25 (s, 3H), 2.03-1.93 (m, 2H), 1.77-1.67 (m, 2H), 1.64-1.55 (m, 2H), 1.34-1.20 (m, 5H)

MS (electrospray): exact mass calculated for $C_{10}H_{22}N_4$, 198.18; m/z found, 199.1 [M+H]+

Example 29

N-[3-(1-methylpiperidin-4-yl)-propyl]-N,N'-di-Boc-methylisothiourea

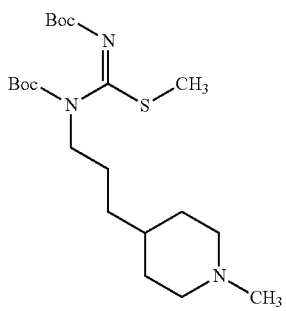 [SMILES: CS/C(=N/C(=O)OC(C)(C)C)N(CCCC1CCN(C)CC1)C(=O)OC(C)(C)C]

To a 25 mL round bottom flask were added 3-(1-methylpiperidin-4-yl)-propan-1-ol (0.23 g, 0.0014 mol), 1,3-di-Boc-2-methylisothiourea (0.42 g, 0.0014 mol), PPh$_3$ (0.42 g, 0.0016 mol) and THF (anhydrous, 8.0 mL). The resultant, stirred stirring solution was cooled to 2.0° C. To the resultant solution was then added DEAD (0.27 mL, 0.0016 mol) drop wise. The reaction was aged cold for 30 min, warmed to room temperature and aged for 14 h. The THF was removed via rotovap and the residue taken up in MTBE (10 mL). The resultant solution was extracted with saturated aqueous NaHCO$_3$ (2×10 mL) and diluted with hexanes (20 mL). After 10 min, the resultant slurry was filtered and the filtrate concentrated via rotovap. The residue was taken up in hexanes (25 mL) and filtered after 10 min. The filtrate was concentrated to yield N-[3-(1-methylpiperidin-4-yl)-propyl]-N,N'-di-Boc-methylisothiourea.

$^1$H-NMR: (400 MHz, CDCl$_3$) δ, 3.50-3.43 (m, 2H), 2.87-2.79 (m, 2H), 2.40 (s, 3H), 2.24 (s, 3H), 1.86 (t, J=10.9 Hz, 2H), 1.72-1.60 (m, 4H), 1.53-1.45 (m, 18H), 1.28-1.20 (m, 5H).

MS (electrospray): exact mass calculated for $C_{21}H_{39}N_3O_4S$, 429.27; m/z found, 430.2 [M+H]+

Example 30

N-[3-(1-methylpiperidin-4-yl)-propyl]-N,N'-di-Boc-guanidine

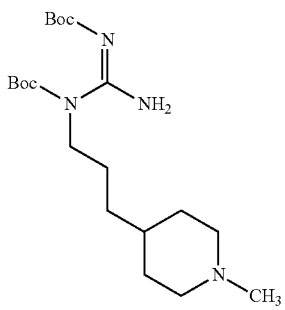

To a 50 mL round bottom flask were added N-[3-(1-methylpiperidin-4-yl)-propyl]-N,N'-di-Boc-methylisothiourea prepared as in Example 29 above (0.57 g, 0.0013 mol) and 2.0 M NH$_3$ in methanol (10 mL). The resultant mixture was aged with stirring for 24 h. The solvent was removed via rotovap to yield a 4:1 mixture of N-[3-(1-methylpiperidin-4-yl)-propyl]-N,N'-di-Boc-guanidine and N-[3-(N-methyl-4-piperidinyl)-1-propyl]guanidine.

Example 31

N-[3-(1-methylpiperidin-4-yl)-propyl]-N,N''-di-Boc-guanidine

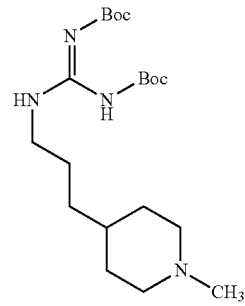

To a 25 mL round bottom flask were added 3-(1-methylpiperidin-4-yl)-propylamine, 1,3-di-Boc-2-methylisothiourea and methanol (10 mL). The resultant mixture was aged at room temperature for 2.0 h, then heated to reflux, at which temperature ~90% of the solvent was removed by distillation. The resultant residue was cooled to room temperature and partitioned between 1 N NaOH (20 mL) and ethyl acetate (20 mL). The layers were separated and the aqueous layer was extracted with ethyl acetate (1×20 mL). All organic layers were combined, dried over anhydrous MgSO$_4$, filtered and concentrated to yield N-[3-(1-methylpiperidin-4-yl)-propyl]-N,N''-di-Boc-guanidine (0.80 g, 106%).

$^1$H-NMR: (400 MHz, CDCl$_3$) δ, 11.5 (brs, 1H), 8.32 (brs, 1H), 3.39 (dt, J=12.9 Hz, J=6.6 Hz, 2H), 2.89-2.82 (m, 2H), 2.24 (s, 3H), 1.90 (t, J=10.9 Hz, 2H), 1.71-1.45 (m, 22H), 1.32-1.20 (m, 5H).

MS (electrospray): exact mass calculated for $C_{20}H_{38}N_4O_4$, 398.29; m/z found, 399.2 [M+H]+

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (XII)

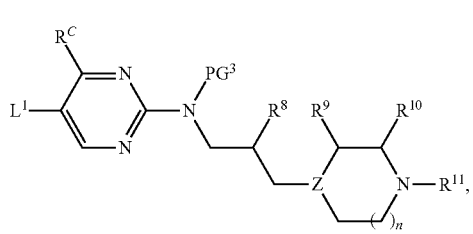

(XII)

wherein
PG³ is a nitrogen protecting group selected from the group consisting of: —C(O)O—C(CH₃)₃, —C(O)—CH₃ and —C(O)O—CH₂CH₃;
L¹ is CN;
Rᶜ is selected from the group consisting of H, methyl, ethyl, propyl, isopropyl, —CF₃, cyclopropyl, and cyclobutyl;
R⁸ is selected from the group consisting of hydrogen and $C_{1-4}$alkyl;
Z is selected from the group consisting of N and CH;
n is 1 or 2;
R⁹, R¹⁰ and R¹¹ are each independently selected from the group consisting of hydrogen and $C_{1-4}$alkyl;
or a pharmaceutically acceptable salts thereof.

2. A compound as in claim 1, wherein the compound of formula (XII) is a compound of formula (XII-S)

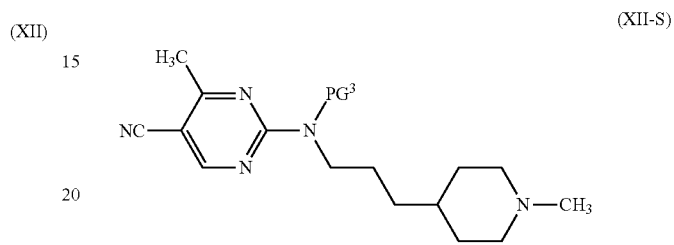

(XII-S)

or a pharmaceutically acceptable salt thereof.

3. A compound as in claim 2, wherein PG³ is selected from the group consisting of —C(O)OCH₂CH₃ and —C(O)OC(CH₃)₃.

* * * * *